United States Patent
Kontani et al.

(10) Patent No.: US 6,949,543 B2
(45) Date of Patent: Sep. 27, 2005

(54) AMIDE DERIVATIVE

(75) Inventors: Toru Kontani, Tsukuba (JP); Junji Miyata, Tsukuba (JP); Wataru Hamaguchi, Tsukuba (JP); Yoji Miyazaki, Tsukuba (JP); Hiroshi Suzuki, Tsukuba (JP); Eiichi Nakai, Tsukuba (JP); Shunji Kageyama, Itabashi-ku (JP)

(73) Assignees: Yamanouchi Pharmaceutical Co., Ltd., Tokyo (JP); Rational Drug Design Laboratories, Tokyo (JP)

( * ) Notice: Subject to any disclaimer, the term of this patent is extended or adjusted under 35 U.S.C. 154(b) by 22 days.

(21) Appl. No.: 10/416,371

(22) PCT Filed: Nov. 8, 2001

(86) PCT No.: PCT/JP01/09790
§ 371 (c)(1),
(2), (4) Date: May 12, 2003

(87) PCT Pub. No.: WO02/38554
PCT Pub. Date: May 16, 2002

(65) Prior Publication Data
US 2004/0034232 A1 Feb. 19, 2004

(30) Foreign Application Priority Data
Nov. 10, 2000 (JP) ......................................... 2000-344354

(51) Int. Cl.[7] ..................... A61K 31/426; C07D 277/40

(52) U.S. Cl. ...................... 514/230.5; 544/52; 544/105; 546/165; 546/209; 548/201; 548/202; 548/181; 548/127; 548/198; 548/178; 514/367; 514/365; 514/361; 514/326; 514/224.2

(58) Field of Search ................................. 548/201, 202, 548/181, 127, 198, 178; 546/165, 209; 544/52, 105; 514/367, 365, 361, 326, 224.2, 230.5

(56) References Cited

U.S. PATENT DOCUMENTS 6,057,451 A * 5/2000 Crute et al. ................. 548/194

* cited by examiner

Primary Examiner—Laura L. Stockton
(74) Attorney, Agent, or Firm—Sughrue Mion, PLLC

(57) ABSTRACT

The invention relates to a novel amide derivative which is an N-({[4-(substituted thiazol-4-yl)phenyl]carbamoyl}methyl) amide derivative having a characteristic in that an aryl or heteroaryl group as an aromatic ring group is directly substituted on the N atom of amido group. Since said amide derivative has excellent anti-herpesvirus action, it is useful as medicaments and antiviral agents, particularly as preventive or therapeutic agents for various diseases accompanied by Herpesviridae virus infections, illustratively, varicella (chickenpox) accompanied by varicella zoster virus infection, shingles accompanied by the recurrent infection of latent varicella zoster virus, labial herpes and herpes encephalitis accompanied by HSV-1 infection, genital herpes accompanied by HSV-2 and the like various herpesvirus infections.

8 Claims, No Drawings

AMIDE DERIVATIVE

TECHNICAL FIELD

This invention relates to a novel amide derivative or a salt thereof useful as medicaments and antiviral agents, particularly for the prevention and treatment of diseases in which varicella zoster virus or the like herpesvirus is concerned.

BACKGROUND OF THE INVENTION

Viruses belonging to the Herpesviridae family cause various infectious diseases in human and animals. For example, it is known that *varicella zoster* virus (VZV) causes *varicella* and shingles, and herpes simplex virus type 1 and 2 (HSV-1 and HSV-2) cause herpes labialis, genital herpes and the like infections, respectively. In addition, infectious diseases caused by cytomegalovirus (CMV), EB virus (Epstein-Barr virus; EBV), human herpesviruses 6, 7 and 8 and the like herpesviruses have also been revealed in recent years.

Currently, acyclovir (ACV), its prodrugs varacyclovir (VCV) and fancyclovir (FCV) and the like nucleoside analogues are used as anti-herpesvirus drugs for VZV and HSV. These nucleoside analogues drugs are mono-phosphorylated into nucleoside monophosphate by viral thymidine kinase encoded by VZV and HSV and then converted into triphosphate compounds by cellular enzymes. Finally, the tri-phosphorylated nucleoside analogues are incorporated during the replication of viral genomic DNA by herpesvirus DNA polymerase and inhibit elongation reaction of viral DNA chains. Thus, since the reaction mechanism of existing anti-herpesvirus agents is based on the "competitive inhibition" for deoxynucleoside triphosphate, it is necessary to use these drugs in a high concentration in order to exert their antiviral effects. Actually, it is the present situation that these anti-herpes nucleoside analogues are administered in a high dosage of from several hundred mg to several g as their clinical dose. In addition, since nucleoside analogues are able to incorporate into host genomic DNA by DNA polymerase of the host, there is some apprehension about their mutagenicity.

On the other hand, some drugs which are non-nucleoside analogues and show anti-herpesvirus activity have recently been reported. For example, WO 97/24234 discloses amide or sulfonamide derivatives represented by the following formula (G) wherein an N atom is substituted with thiazolylphenylcarbamoylmethyl group or the like, which shows anti-HSV-1 activity and anti-CMV activity by inhibiting an HSV helicase-primase enzyme complex. However, the anti-VZV activity of these compounds is not illustratively disclosed.

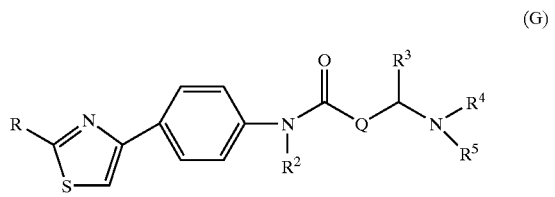

(G)

(In the formula, R is hydrogen, lower alkyl, amino, lower alkylamino or the like, $R^2$ is hydrogen or lower alkyl, Q is not present or methylene, $R^3$ is hydrogen, lower alkyl or the like, $R^4$ is unsubstituted or substituted phenyl(lower) alkyl, 1-indanyl, 2-indanyl, (lower cycloalkyl)-(lower alkyl), (Het)-(lower alkyl) or the like, $R^5$ is phenylsulfonyl, 1- or 2-naphthylsulfonyl, (Het)-sulfonyl, (unsubstituted or substituted phenyl)-Y—($CH_2$)nC(O), (Het)-($CH_2$)nC(O) or the like, Y is O or S, and n is 0, 1 or 2. See said document for details.)

WO 00/29399 also discloses amide or sulfonamide derivatives represented by the following formula (H) wherein an N atom is substituted with thiazolylphenylcarbamoylmethyl group, which shows anti-HSV-1 activity and anti-CMV activity, but the anti-VZV activity of these compounds is not illustratively disclosed.

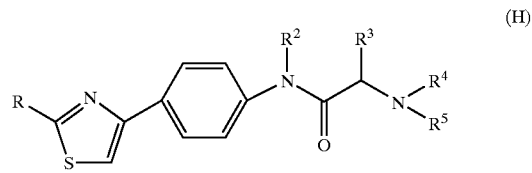

(H)

(In the formula, $R^1$ is $NH_2$, $R^2$ is H, $R^3$ is H, $R^4$ is $CH_2Ph$, $CH_2$-(4-pyridyl), $CH_2$-cyclohexyl or the like, and $R^5$ is CO-(substituted phenyl), CO-(unsubstituted or substituted hetero ring) or the like. See said document for details.)

In addition, recently, there are reports on various herpesvirus protease inhibitors (Waxman Lloid et al., 2000, *Antiviral Chemistry and Chemotherapy*, 11, 1–22) and N-(carbonylphenyl)benzamide derivatives as HSV primase inhibitors (WO 00/58270). However, these documents do not disclose compounds having good anti-VZV activity, too.

Development of a non-nucleoside analogue anti-herpesvirus agent having sufficient anti-VZV activity and also having high safety is in great demand.

DISCLOSURE OF THE INVENTION

As a result of intensive studies on compounds having anti-varicella zoster virus (anti-VZV) activity, the present inventors have accomplished the invention by finding that novel amide derivatives (including sulfonamide derivatives) characterized in that, as shown in the following general formula (I), an aryl group or heteroaryl group as an aromatic ring group is directly, without mediating alkylene chain, substituted as the group A on an amido group in which the N atom is substituted with thiazolylphenylcarbamoylmethyl group have excellent anti-VZV activity.

That is, the invention relates to a novel amide derivative represented by the following general formula (I) or a salt thereof.

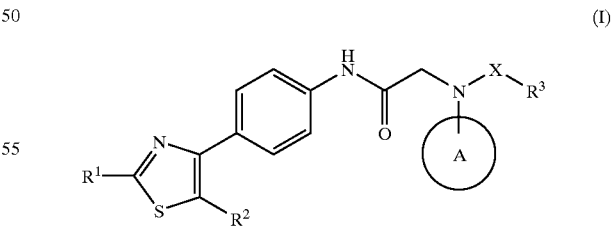

(I)

(Symbols in the formula have the following meanings; $R^1$ and $R^2$: the same or different from each other, and each represents —H, -lower alkyl, -lower alkenyl, -lower alkynyl, -cycloalkyl, -cycloalkenyl, —NRaRb, —NRc-NRaRb, —NRc-(nitrogen-containing saturated heterocyclic ring which may be substituted with lower alkyl), —NRc-C (=NH)—NRaRb, -(nitrogen-containing saturated heterocyclic ring which may be substituted with lower alkyl), -lower alkylene-NRaRb, -lower alkylene-(nitrogen-containing saturated heterocyclic ring which may be substituted with lower alkyl), —NRaCORb, —NRaCO—ORb, —NRaCO—NRbRc, —NRaCO-lower alkylene-NRbRc, —NRaCO-lower alkylene-(nitrogen-containing saturated heterocyclic ring which may be substituted with lower alkyl), —NRaSO$_2$Rb, —NRaSO$_2$—NRbRc, —NRaSO$_2$-lower alkylene-NRbRc, —NRaSO$_2$-lower alkylene-(nitrogen-containing saturated heterocyclic ring which may be substituted with lower alkyl), —CONRaRb, —SO$_2$NRaRb, —COORa, —SO$_2$Ra, —CONRa-ORb, —OCORa, —ORa, -halogen, —CORa, —NO$_2$, —CN or -halogeno lower alkyl, Ra, Rb and Rc: the same or different from one another, and each represents —H, -lower alkyl, -lower alkenyl, -lower alkynyl, -cycloalkyl, -cycloalkenyl, -aryl, -5- or 6-membered monocyclic heteroaryl or -lower alkylene-aryl,
A: -aryl which may have one or more substituents, -heteroaryl which may have one or more substituents, -saturated carbon ring-condensed aryl which may have one or more substituents or -saturated heterocyclic ring-condensed aryl which may have one or more substituents, wherein the saturated carbon ring-condensed aryl and saturated heterocyclic ring-condensed aryl bind to the adjacent N atom via C atom of the aromatic ring,
X: CO or SO$_2$,
R$^3$: -alkyl which may have one or more substituents, -alkenyl which may have one or more substituents, -alkynyl which may have one or more substituents, -cycloalkyl which may have one or more substituents, -cycloalkenyl which may have one or more substituents, -aryl which may have one or more substituents, -hetero ring which may have one or more substituents or
—NRaRb, or it may form a group represented by the following formula together with the adjacent group —N(A)-X—,

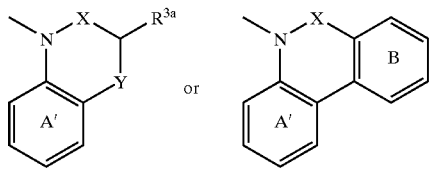

Y: O, S, a bond or CH$_2$,
R$^{3a}$: —H, -cycloalkyl which may have one or more substituents,
-cycloalkenyl which may have one or more substituents, -aryl which may have one or more substituents or -hetero ring which may have one or more substituents, and A' and B: the same or different from each other, and each represents benzene ring which may have one or more substituents. The same shall apply hereinafter.)

In addition, the invention relates to a pharmaceutical composition which contains the amide derivative represented by the aforementioned general formula (I) or a salt thereof and a pharmaceutically acceptable carrier, and an anti-herpesvirus agent, particularly an anti-VZV agent.

The compounds of general formula (I) are further described.

In this specification, the term "lower" means a straight or branched hydrocarbon chain having from 1 to 6 carbon atoms. As the "lower alkyl", it is preferably an alkyl group having from 1 to 4 carbon atoms, particularly preferably methyl, ethyl, n-propyl, isopropyl, n-butyl, isobutyl or tert-butyl group. As the "lower alkenyl", it is preferably an alkenyl group having from 2 to 5 carbon atoms, particularly preferably vinyl, allyl, 1-propenyl, isopropenyl, 1-butenyl, 2-butenyl or 3-butenyl group. As the "lower alkynyl", it is preferably an alkynyl group having from 2 to 5 carbon atoms, particularly preferably ethynyl, 1-propynyl, 2-propynyl, 1-butynyl, 2-butynyl, 3-butynyl or 1-methyl-2-propynyl group. Also, as the "lower alkylene", it is preferably an alkylene group having from 1 to 3 carbon atoms, particularly preferably methylene, ethylene, trimethylene or dimethylmethylene group.

As the "alkyl", it is preferably a straight or branched chain alkyl group having from 1 to 10 carbon atoms, and its further preferred examples include methyl, ethyl, n-propyl, isopropyl, n-butyl, isobutyl, tert-butyl, 1,1-dimethylpropyl, 2,2-dimethylpropyl, 2,2-diethylpropyl, n-octyl and n-decyl groups. As the "alkenyl" and "alkynyl", they are preferably straight or branched chain groups having from 2 to 10 carbon atoms.

As the "aryl", it means an aromatic hydrocarbon ring group and is preferably an aryl group having from 6 to 14 carbon atoms, and phenyl and naphthyl groups are more desirable. As the "cycloalkyl", it is a cycloalkyl group having from 3 to 10 carbon atoms, which may have a cross-link, and preferred are cyclopropyl, cyclopentyl, cyclohexyl, cycloheptyl and adamantyl groups. As the "cycloalkenyl", it is preferably a cycloalkenyl group having from 3 to 10 carbon atoms, and particularly preferred are cyclopentenyl and cyclohexenyl groups. The "saturated carbon ring-condensed aryl" is a condensed ring group in which benzene ring or naphthalene ring is condensed with a C$_{5-6}$ saturated carbon ring, and preferred are indanyl and tetrahydronaphthyl.

The "hetero ring" is a saturated or unsaturated monocyclic or bicyclic or tricyclic 5- to 8-membered hetero ring containing from 1 to 4 hetero atoms selected from N, S and O. Preferred are "heteroaryl", "5- to 8-membered monocyclic saturated heterocyclic ring" and "saturated heterocyclic ring-condensed aryl" which are described in the following.

The "5- or 6-membered monocyclic heteroaryl" is a 5- or 6-membered monocyclic heteroaryl containing from 1 to 4 hetero atoms selected from N, S and O, and preferred are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidinyl, pyridazinyl, pyrazinyl and triazinyl. The "heteroaryl" includes the aforementioned 5- or 6-membered monocyclic heteroaryl and a bi- or tri-cyclic heteroaryl condensed with benzene ring or in which heteroaryl rings are condensed with each other. In this connection, preferred as the monocyclic heteroaryl are those described in the foregoing, and preferred as the bi- or tri-cyclic heteroaryl include benzofuranyl, benzothienyl, benzothiadiazolyl, benzothiazolyl, benzoxazolyl, benzoxadiazolyl, benzoimidazolyl, indolyl, isoindolyl, indazolyl, quinolyl, isoquinolyl, cinnolinyl, quinazolinyl, quinoxalinyl, benzodioxolyl, imidazopyridyl, indolidinyl, carbazolyl, dibenzofuranyl and dibenzothienyl groups.

The "5- to 8-membered monocyclic saturated heterocyclic ring" is a 5- to 8-membered monocyclic saturated heterocyclic ring which contains from 1 to 4 hetero atoms selected from N, S and O and may have a crosslink, and preferred are tetrahydro-2H-pyranyl, tetrahydro-2H-thiopyranyl, thiepanyl, thiocanyl, pyrrodinyl, imidazolidinyl, pyrazolidinyl, piperazinyl, azepanyl, diazepanyl, piperidinyl and morpholinyl groups. Further preferred are 5- to 7-membered ring groups. In addition, the "nitrogen-containing saturated heterocyclic ring" is a group having at least one ring nitrogen atom among the aforementioned "5- to 8-membered monocyclic saturated heterocyclic ring", and its preferred examples include piperidino, morpholino, 1-piperazinyl and 1-pyrolidinyl.

The "saturated heterocyclic ring-condensed aryl" is a group wherein the aforementioned 5- to 8-membered monocyclic saturated heterocyclic ring and benzene ring or naphthalene ring are condensed, and preferred are 3,4-dihydro-2H-1,4-benzoxadinyl, 3,4-dihydro-2H-1,4-benzothiazinyl, 1,3-benzodioxolyl, 2,3-dihydro-1,4-benzodioxynyl, chromanyl, isochromanyl, 3,4-dihydro-2H-1-benzothiopyranyl, 3,4-dihydro-1H-2-benzothiopyranyl, indolinyl, isoindolinyl, 1,2,3,4-tetrahydroquinolyl and 1,2,3,4-tetrahydroisoquinolyl groups.

When the ring A is a "saturated carbon ring-condensed aryl" or a "saturated heterocyclic ring-condensed aryl", the ring A binds to the N atom of adjacent amido group via C atom of the aromatic ring. On the other hand, when $R^3$ is a "saturated heterocyclic ring-condensed aryl", the $R^3$ binds to the adjacent group X via C atom of the aromatic ring or the C atom or N atom of the saturated ring.

As the "halogen", F, Cl, Br and I atoms can be exemplified. The "halogeno lower alkyl" is the aforementioned lower alkyl on which one or more of the above halogen are substituted, and is preferably —$CF_3$.

The substituents in the "alkyl which may have one or more substituents", "alkenyl group which may have one or more substituents" and "alkynyl group which may have one or more substituents" are preferably 1 to 4 substituents selected from the following group C.

Group C: -cycloalkyl, -cycloalkenyl, -aryl, —NRaRb, —NRc-NRaRb, -(nitrogen-containing saturated heterocyclic ring which may have one or more substituents selected from -lower alkyl, -lower alkylene-COORa and —NRaRb), —NRc-(nitrogen-containing saturated heterocyclic ring which may have one or more substituents selected from -lower alkyl, -lower alkylene-COORa and —NRaRb), —O-lower alkylene-NRaRb, —O-lower alkylene-(nitrogen-containing saturated heterocyclic ring which may have one or more substituents selected from -lower alkyl, -lower alkylene-COORa and —NRaRb), —O-lower alkylene-ORa, —O-lower alkyl-COORa, —COORa, -halogen, —CORa, —$NO_2$, —CN, —ORa, —O-(halogeno lower alkyl, —SRa, —SORa, —$SO_2$Ra, —CO—NRaRb, —CO-(nitrogen-containing saturated heterocyclic ring which may have one or more substituents selected from -lower alkyl, -lower alkylene-COORa and —NRaRb), —NRa-CORb, —$SO_2$NRaRb and =O (oxo) (wherein Ra, Rb and Rc are as described in the above).

The substituents in "the cycloalkyl which may have one or more substituents", "cycloalkenyl which may have one or more substituents", "aryl which may have one or more substituents", "saturated carbon ring-condensed aryl which may have one or more substituents", "heteroaryl which may have one or more substituents", "saturated heterocyclic ring-condensed aryl which may have one or more substituents", "5- to 8-membered hetero ring which may have one or more substituents" and "benzene ring which may have one or more substituents" are preferably 1 to 5 substituents selected from the following group D.

Group D: -(lower alkyl which may have one or more substituents selected from —ORa, —SRa, —CN, —COORa, —CONRaRb, —NRaRb and -(nitrogen-containing saturated heterocyclic ring which may have one or more substituents selected from -lower alkyl, -lower alkylene-COORa and —NRaRb)), -lower alkenyl, -lower alkynyl, -halogeno lower alkyl, 5- or 6-membered monocyclic heteroaryl and the substituents described in the above group C.

Further preferred are 1 to 4 substituents selected from the following group D1.

Group D1: -lower alkyl, -phenyl, -halogeno lower alkyl, —COOH, —COO-lower alkyl, -halogen, —$NO_2$, —CN, —OH, —O-lower alkyl, —O-halogeno lower alkyl, —O-lower alkylene-O-lower alkyl, —O-lower alkylene-COOH, —O-lower alkylene-COO-lower alkyl, —O-lower alkylene-$NH_2$, —O-lower alkylene-NH-lower alkyl, —O-lower alkylene-N(lower alkyl)$_2$, —O-lower alkylene-(nitrogen-containing saturated heterocyclic ring which may be substituted with lower alkyl), $NH_2$, —NH-lower alkyl, —N(lower alkyl)$_2$, -(nitrogen-containing saturated heterocyclic ring which may have one or more substituents selected from -lower alkyl and -lower alkylene-COORa), —NHCO-lower alkyl, —N(lower alkyl)CO-lower alkyl, —CONH$_2$, —CONH-lower alkyl, —CON(lower alkyl)$_2$, =O(oxo), —SH, —S-lower alkyl, —SO-lower alkyl and —$SO_2$-lower alkyl groups.

A compound including S atom-containing saturated heterocyclic ring may form an oxide (SO) or dioxide ($SO_2$) compound by substitution of 1 or 2 =O(oxo) on said S atom.

As the group formed from $R_3$ together with the adjacent group —N(A)-X—, the following groups can be preferably cited.

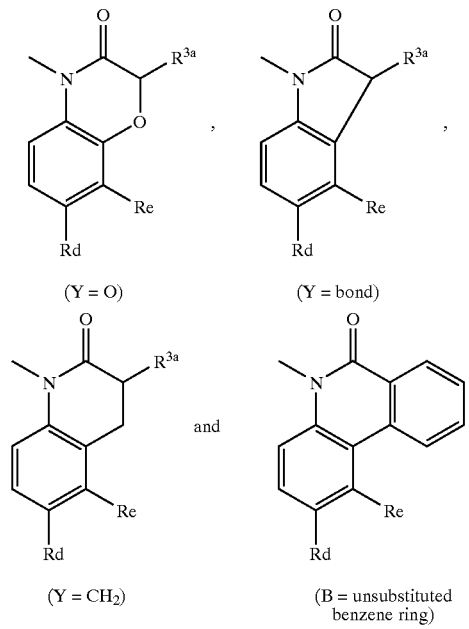

(In the formula, $R^{3a}$ is —H, or cycloalkyl, cycloalkenyl, aryl, saturated carbon ring-condensed aryl, saturated heterocyclic ring-condensed aryl, heteroaryl or 5- to 8-membered monocyclic saturated heterocyclic ring, which may be substituted with 1 to 4 substituents selected from the group D1, and Rd and Re may be the same or different from each other and each represents —H, -lower alkyl, -halogen, —OH or —O-lower alkyl.)

Among compounds (I) of the invention, preferred compounds are shown below.

1. A compound in which $R^1$ and $R^2$ may be the same or different from each other and each represents —H, -lower alkyl, -lower alkenyl, -lower alkynyl, —NRaRb, —NRc-NRaRb, -(nitrogen-containing saturated heterocyclic ring which may be substituted with lower alkyl), —NRc-C(=NH)—NRaRb, —NRaCORb, —NRaCO—ORb, —NRaCO—NRbRc, —NRaCO-lower alkylene-NRbRc or —NRaCO-lower alkylene-(nitrogen-containing saturated heterocyclic ring which may be substituted with lower alkyl), A is aryl which may have 1 to 5 substituents selected from the group D, heteroaryl which may have 1 to 5 substituents selected from the group D, saturated carbon ring-condensed aryl which may have 1 to 5 substituents selected from the group D or saturated heterocyclic ring-condensed aryl which may have 1 to 5 substituents selected from the group D, and $R^3$ is cycloalkyl which may have 1 to 5 substituents selected from the group D, cycloalkenyl which may have 1 to 5 substituents selected from the group D, aryl which may have 1 to 5 substituents selected from the group D, saturated heterocyclic ring-condensed aryl which may have 1 to 5 substituents selected from the group D, heteroaryl which may have 1 to 5 substituents selected from the group D or 5- to 8-membered monocyclic saturated heterocyclic ring which may have 1 to 5 substituents selected from the group D.

2. A compound in which A is an aryl selected from phenyl and naphthyl; a heteroaryl selected from benzofuranyl, benzothienyl, benzothiadiazolyl, benzothiazolyl, benzoxazolyl, benzoxadiazolyl, benzoimidazolyl, indolyl, isoindolyl, indazolyl, quinolyl, isoquinolyl, cinnolinyl, quinazolinyl, quinoxalinyl, benzodioxolyl, imidazopyridyl and indolidinyl groups; a saturated carbon ring-condensed aryl selected from 4-indanyl, 5-indanyl, 5,6,7,8-tetrahydronaphthalen-1-yl and 5,6,7,8-tetrahydronaphthalen-2-yl; or a saturated heterocyclic ring-condensed aryl selected from 3,4-dihydro-2H-1,4-benzoxadinyl, 3,4-dihydro-2H-1,4-benzothiazinyl, 1,3-benzodioxolyl, 2,3-dihydro-1,4-benzodioxynyl, chromanyl, isochromanyl, 3,4-dihydro-2H-1-benzothiopyranyl, 3,4-dihydro-1H-2-benzothiopyranyl, indolinyl, isoindolinyl, 1,2,3,4-tetrahydroquinolyl and 1,2,3,4-tetrahydroisoquinolyl groups, wherein the aforementioned aryl, heteroaryl, saturated carbon ring-condensed aryl or saturated heterocyclic ring-condensed aryl may have 1 to 4 substituents respectively selected from the group D1, and $R^3$ is cycloalkyl which may have 1 to 4 substituents selected from the group D1, cycloalkenyl which may have 1 to 4 substituents selected from the group D1, aryl which may have 1 to 4 substituents selected from the group D1,saturated carbon ring-condensed aryl which may have 1 to 4 substituents selected from the group D1, heteroaryl which may have 1 to 4 substituents selected from the group D1, or 5- to 8-membered monocyclic saturated heterocyclic ring which may have 1 to 4 substituents selected from the group D1.

3. A compound in which A is aryl which may have 1 to 4 substituents selected from the group D1, heteroaryl which may have 1 to 4 substituents selected from the group D1 or saturated heterocyclic ring-condensed phenyl which may have 1 to 4 substituents selected from the group D1, and $R^3$ is cycloalkyl which may have 1 to 4 substituents selected from the group D1, cycloalkenyl which may have 1 to 4 substituents selected from the group D1, aryl which may have 1 to 4 substituents selected from the group D1, saturated heterocyclic ring-condensed phenyl which may have 1 to 4 substituents selected from the group D1 or 5- to 7-membered monocyclic saturated heterocyclic ring which may have 1 to 4 substituents selected from the group D1.

4. A compound in which X is CO.
5. A compound in which $R^1$ is —$NH_2$ and $R^2$ is —H.
6. A compound in which A is a group selected from phenyl, benzothienyl, benzothiadiazolyl, benzothiazolyl, indolyl, quinolyl and 5-indanyl, which may have 1 or 2 substituents selected from the group consisting of -lower alkyl, —$CF_3$, -halogen, —OH, —SH, —S-lower alkyl and —O-lower alkyl; or a group selected from 3,4-dihydro-2H-1,4-benzoxadinyl, 3,4-dihydro-2H-1,4-benzothiazinyl, 1,3-benzodioxolyl, 2,3-dihydro-1,4-benzodioxynyl and indolyl groups, which may be substituted with 1 or 2 =O(oxo), and $R^3$ is a group selected from cyclohexyl, cyclohexenyl, phenyl, pyridyl, pyrimidinyl, quinolyl and tetrahydro-2H-pyranyl, which may be substituted with 1 or 2 halogen atoms; or a group selected from tetrahydro-2H-thiopyranyl and 3,4-dihydro-2H-1-benzothiopyranyl, which may be substituted with 1 or 2 oxo groups.

7. Compounds listed below or salts thereof.
N-({[4-(2-Aminothiazol-4-yl)phenyl]carbamoyl}methyl)-4-fluoro-N-(2,3-dihydro-1H-indol-6-yl)benzamide,
N-({[4-(2-aminothiazol-4-yl)phenyl]carbamoyl}methyl)-4-fluoro-N-(1,2,3,4-tetradihydroquinolin-6-yl)benzamide,
N-({[4-(2-aminothiazol-4-yl)phenyl]carbamoyl}methyl)-N-(2,3-dihydro-1,4-benzodioxin-6-yl)-4-fluorobenzamide,
N-({[4-(2-aminothiazol-4-yl)phenyl]carbamoyl}methyl)-N-(1,3-benzodioxol-5-yl)-4-fluorobenzamide,
N-({[4-(2-aminothiazol-4-yl)phenyl]carbamoyl}methyl)-N-benzothiazol-5-yl-4-fluorobenzamide,
N-({[4-(2-aminothiazol-4-yl)phenyl]carbamoyl}methyl)-N-benzothiazol-6-yl-4-fluorobenzamide,
N-({[4-(2-aminothiazol-4-yl)phenyl]carbamoyl}methyl)-4-fluoro-N-indan-5-ylbenzamide,
N-({[4-(2-aminothiazol-4-yl)phenyl]carbamoyl}methyl)-4-fluoro-N-(3-hydroxyindan-5-yl)benzamide,
N-({[4-(2-aminothiazol-4-yl)phenyl]carbamoyl}methyl)-4-fluoro-N-(1H-indol-5-yl)benzamide,
N-({[4-(2-aminothiazol-4-yl)phenyl]carbamoyl}methyl)-4-fluoro-N-(3-oxo-3,4-dihydro-2H-1,4-benzothiazin-6-yl)benzamide,
N-({[4-(2-aminothiazol-4-yl)phenyl]carbamoyl}methyl)-4-fluoro-N-(3-oxo-3,4-dihydro-2H-1,4-benzooxazin-6-yl)benzamide,
N-({[4-(2-aminothiazol-4-yl)phenyl]carbamoyl}methyl)-N-(1,2,3-benzothiadiazol-5-yl)-4-fluorobenzamide,
N-({[4-(2-aminothiazol-4-yl)phenyl]carbamoyl}methyl)-N-(4-methoxyphenyl)tetrahydro-2H-thiopyran-4-carboxamide 1,1-dioxide,
N-({[4-(2-aminothiazol-4-yl)phenyl]carbamoyl}methyl)-N-benzothiazol-5-yl-4-fluorocyclohex-3-enecarboxamide,
N-({[4-(2-aminothiazol-4-yl)phenyl]carbamoyl}methyl)-N-benzothiazol-5-yl-4,4-difluorocyclohexanecarboxamide, and
N-({[4-(2-aminothiazol-4-yl)phenyl]carbamoyl}methyl)-N-indan-5-yltetrahydro-2H-thiopyran-4-carboxamide 1,1-dioxide.

Salts of the compound (I) of the invention are pharmaceutically acceptable salts. Illustrative examples of its acid addition salt include acid addition salts with hydrochloric acid, hydrobromic acid, hydroiodic acid, sulfuric acid, nitric acid, phosphoric acid and the like inorganic acids, and with formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like organic acids. In addition, there is a case of forming salts with bases depending on the kinds of substituents, and their examples include salts with inorganic bases containing sodium, potassium, magnesium, calcium, aluminum and the like metals, salts with methylamine, ethylamine, ethanolamine, lysine, ornithine and the like organic bases, ammonium salts and the like.

Depending on the kinds of substituents, there is a case in which the compound (I) of the invention exists, e.g., in cis-trans and the like geometrical isomers or keto-enol and the like tautomers, and separated or mixed substances of these isomers are included in the invention. Also, since the compound of the invention contains asymmetric carbon atom in some cases, isomers based on the asymmetric carbon atom can exist. The invention also includes mixtures and isolated forms of these optical isomers. Also, depending on the kinds of substituents, there is a case in which the compound of the invention forms N-oxide, and these N-oxide compounds are also included in the invention. In addition, the invention also includes various hydrates, solvates and polymorphic substances of the compound (I) of the invention. In this connection, all of the compounds which are metabolized in the living body and converted into compounds having the aforementioned general formula (I) or salts thereof, so-called prodrugs, are included in the compound of the invention. As groups which form the prodrugs of the invention, those groups described in Prog. Med., 5: 2157–2161 (1985) and those described in "Iyakuhin-no Kaihatsu (Development of Drugs)", Vol. 7, Bunshi Sekkei (Molecular Designing), 163–198, published in 1990 by Hirokawa Shoten can be exemplified.

(Production Methods)

Typical production methods of the compound (I) of the invention are described in the following.

In this connection, depending on the kinds of functional group in the following production methods, there is a case in which substitution of said functional group by an appropriate protecting group, namely a group which can be easily converted into said functional group, at the stage of the material or its intermediate is effective in view of the production techniques. Thereafter, a compound of interest can be obtained by removing the protecting group as occasion demands. Amino group, hydroxyl group, carboxyl group and the like can be exemplified as such functional groups, and as their protecting groups, the protecting groups described in Protective Groups in Organic Synthesis, 3rd Edition (edited by T. W. Green and P. G. M. Wuts, published by JOHN WILLY & SONS, INC.) can for example be cited, which may be optionally used depending on the reaction conditions. The methods described in said textbook can be optionally applied to the introduction of protecting groups and deprotection.

Production method 1

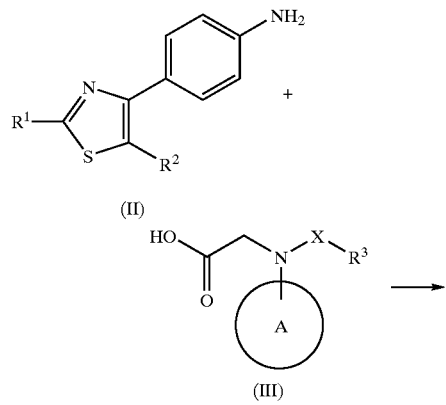

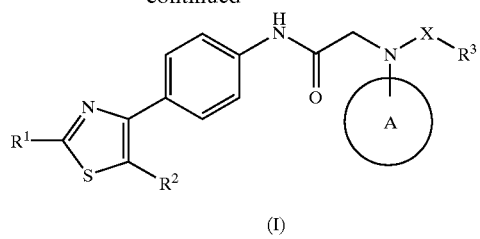

(I)

The compound (I) of the invention can be easily produced by subjecting a carboxylic acid compound (III) and a thiazolylphenyl derivative (II) to amidation reaction.

The amidation reaction can be carried out by a conventional method, for example, a method described in "Jikken Kagaku Koza (Experimental Chemistry Course)" 4th Edition (Maruzen), vol. 22, pp. 137–173, edited by The Chemical Society of Japan, can be employed. Preferably, it can be carried out by converting the carboxylic acid compound (III) into a reactive derivative such as an acid halide (acid chloride or the like) or acid anhydride and then allowing it to react with the thiazolylphenyl derivative (II). When a reactive derivative of the carboxylic acid is used, it is desirable to add a base (sodium hydroxide or the like inorganic base or triethylamine (TEA), diisopropylethylamine, pyridine or the like organic base). In addition, the amidation can also be carried out in the presence of a carboxylic acid activating agent for the carboxylic acid, such as a condensing agent (1-ethyl-3-(3-dimethylaminopropyl)carbodiimide (WSC), 1,1'-carbonylbis-1H-imidazole (CDI) or the like). The reaction temperature can be optionally selected depending on the material compounds. Examples of the solvent include reaction-inert solvents such as aromatic hydrocarbon solvents (benzene, toluene and the like), ether solvents (tetrahydrofuran (THF), 1,4-dioxane and the like), halogenated hydrocarbon solvents (dichloromethane, chloroform and the like), amide solvents (N,N-dimethylformamide (DMF), N,N-dimethylacetamide and the like) and basic solvents (pyridine and the like). The solvents are optionally selected based on the kinds of the material compounds and the like, and used alone or as a mixture of two or more.

Production method 2

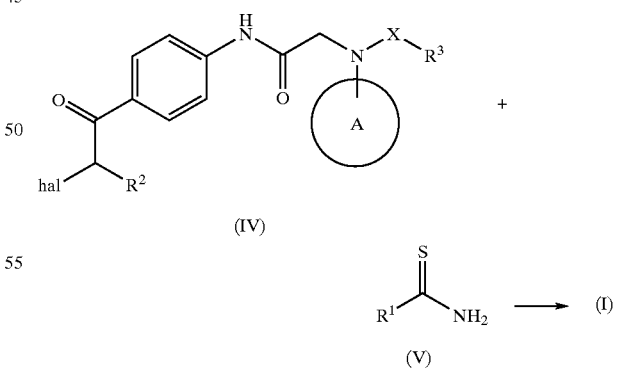

(In the formula, hal represents halogen. The same shall apply hereinafter.)

This production method is a method in which the compound (I) of the invention is obtained by subjecting an α-ketone halide represented by the general formula (IV) to cyclization reaction with a compound (V). This cyclization reaction can be carried out by a conventional method, and the methods described, e.g., in *Tetrahedron Lett.*, 9, 24, 1959, and The Chemistry of Heterocyclic Compounds "Thiazole and its Derivatives 1 and 2" (edited by J. V. Metzger: John Eiley & Sons) can be employed.

Preferably, it can be carried out by allowing the material compound α-ketone halide (IV) to react with the compound (V) under cooling to under heating in a solvent or without using solvent. As the solvent, alcohol solvents (methanol, ethanol, isopropanol and the like), carbonyl solvents (acetone, methyl ethyl ketone and the like) and the aforementioned ether solvents, halogenated hydrocarbon solvents and amide solvents and the like can be used preferably. These solvents may be used alone or as a mixture of two or more. The solvent should be optionally selected depending on the kinds of the material compound and the like. When a base (potassium carbonate, sodium carbonate, TEA or the like) is added in carrying out the reaction, the reaction may progress smoothly in some cases.

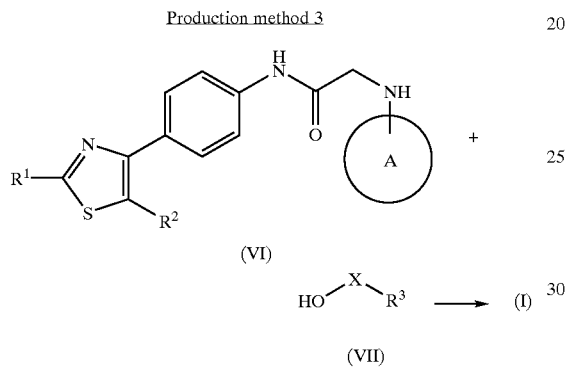

This production method is a method in which the compound (I) of the invention is obtained by subjecting an amine compound represented by the general formula (VI) and a carboxylic acid or sulfonic acid compound (VII) to amidation or sulfonamidation reaction.

The amidation reaction can be carried out in the same manner as in the production method 1.

The sulfonamidation reaction can be carried out in the usual way by allowing a sulfonic acid reactive derivative of the compound (VII) to react with the amine compound (VI). As the reactive derivative of sulfonic acid, an acid halide (acid chloride, acid bromide or the like), an acid anhydride (sulfonic anhydride prepared from two molecules of sulfonic acid), an acid azide and the like can be exemplified. These reactive derivatives of sulfonic acid can be obtained easily from corresponding sulfonic acids in accordance with a usually used general method. When an acid halide is used as the reactive derivative, it is desirable to carry out the reaction in the presence of a base (sodium hydroxide, sodium hydride or the like inorganic base or pyridine, TEA, diisopropylethylamine or the like organic base). When reacted with an acid anhydride, acid azide or the like reactive derivative, the reaction can be carried out in the absence of a base. In some cases, the reaction may be carried out in the presence of sodium hydride or the like inorganic base or TEA, pyridine, 2,6-lutidine or the like organic base. The reaction temperature is optionally selected depending on the kinds of the sulfonic acid reactive derivative and the like. As the solvent, a reaction inert solvent such as the solvent exemplified for the amidation of the aforementioned production method 1 can be used.

In addition, depending on the kinds of substituents, a desired compound of the invention can be produced by further subjecting to a substituent group modification reaction well known to those skilled in the art. For example, known reactions such as the aforementioned amidation and sulfonamidation and the N-alkylation described in "Jikken Kagaku Koza (Maruzen), published by The Chemical Society of Japan, can be optionally employed. Also, the reaction sequence may be optionally changed depending on the compound of the interest and kinds of reaction to be employed.

Production Methods of Material Compounds

Each of the aforementioned material compounds can be easily produced by using known reactions, e.g., the reactions described in "Jikken Kagaku Koza (Maruzen), published by The Chemical Society of Japan. Their typical production methods are shown below.

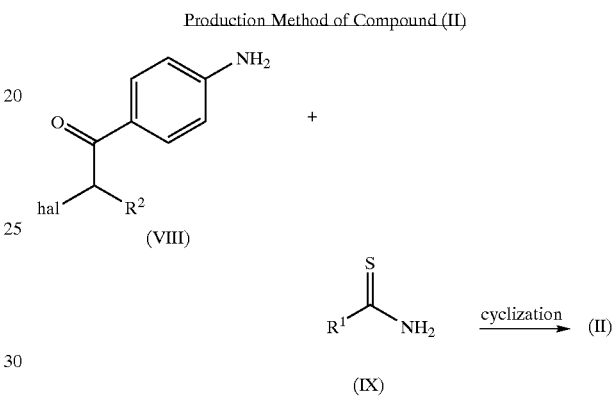

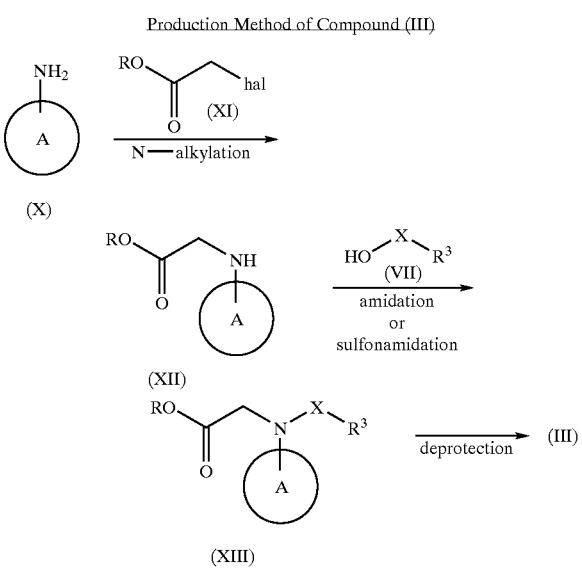

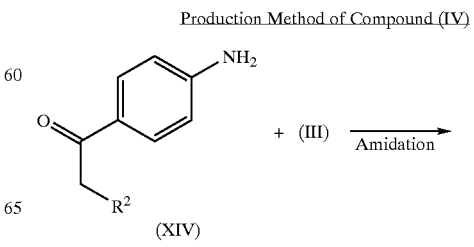

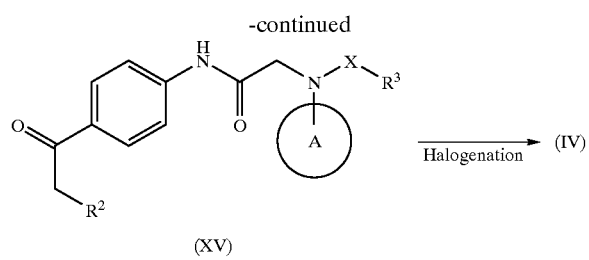

(In the formulae, R means a group which can form an ester residue such as a lower alkyl, aralkyl or the like, and P means an amino group-protecting group such as fluorenylmethoxycarbonyl (Fmoc) or the like.)

In the above reaction schemes, the amidation can be carried out in the same manner as the method described in the aforementioned production method 1, and the cyclization in the same manner as the method described in the production method 2, and the sulfonamidation in the same manner as the method described in the production method 3.

The N-alkylation of compound (X) can be carried out using an alkyl halide compound (XI) by a conventional method such as the method described in the aforementioned "Jikken Kagaku Koza, 4th edition (Maruzen), vol. 20, pp. 279–318. The reaction can be carried out at a reaction temperature of from cooling to heating, and examples of the solvent include reaction-inert solvents such as the solvents exemplified for the amidation in the aforementioned production method 1. It is desirable to carry out the reaction in the presence of potassium carbonate, sodium hydroxide, sodium hydride or the like base.

The deprotection for obtaining the carboxylic acid compound (III) can be carried out by optionally employing a conventional method depending on the kinds of ester. Preferably, it can be carried out by treating with a base such as sodium hydroxide aqueous solution in the case of ethyl ester or the like alkyl ester, or by reducing with palladium-carbon (Pd—C) in an atmosphere of hydrogen in the case of benzyl ester or the like aralkyl ester. The reaction can be carried out in accordance with the aforementioned method described in Protective Groups in Organic Synthesis, 3rd Edition.

The α-ketone halide compound (IV) can be synthesized by the halogenation of an acyl compound (XV) in the usual way. Examples of the halogenation reagent include chlorine, bromine, iodine, copper(II) bromide, potassium iodate, benzyltrimethylammonum tribromide, phenyltrimethylammonium tribromide, tetrabutylammonium tribromide, sulfuryl chloride, trimethylsilyl chloride, trimethylsilyl bromide, 5,5-dibromobarbituric acid and the like, and examples of the solvent include reaction-inert solvents such as acetic acid, hydrobromic acid/acetic acid and the like acidic solvents and the aforementioned alcohol solvents and ether solvents. The reaction can be carried out at a reaction temperature of from cooling to heating.

The deprotection for obtaining the amine compound (VI) can be carried out by optionally employing a conventional method depending on the kinds of protecting groups. For example, the method described in the aforementioned Protective Groups in Organic Synthesis, 3rd Edition, 503–572, can be employed.

In addition, depending on the kinds of substituents, a desired material compound can be produced by further subjecting to a substituent group modification reaction well known to those skilled in the art.

The compound of the invention obtained in this manner is isolated and purified directly as its free form or as a salt thereof after carrying out a salt formation treatment by a conventional method. The isolation and purification are carried out by employing extraction, evaporation, crystallization, filtration, recrystallization, various chromatographic techniques and the like general chemical operations.

Various isomers can be isolated by conventional methods making use of the difference in physicochemical properties between isomers. For example, a racemic compound can be converted into a three-dimensionally pure isomer by a general optical resolution method [e.g., a method in which it is converted into a diastereomer salt with a general optically active acid (tartaric acid or the like) and then subjected to optical resolution]. Also, a mixture of diastereomers can be separated, for example, by fractional crystallization or a chromatography. In addition, an optically active compound can also be produced by the use of an appropriate optically active material.

INDUSTRIAL APPLICABILITY

Since the compound (I) of the invention has excellent anti-VZV activity, it is useful as a medicament, particularly as an anti-herpesvirus agent or the like viral agent, for the prevention or treatment of varicella (chickenpox) accompanied by VZV infection and shingles accompanied by the recurrent infection of latent VZV.

In addition, since the compound of the invention also has the activity to inhibit replication of other herpesviruses (HSV-1, HSV-2 and the like), it can also be applied to the prevention or treatment of various herpesvirus infections such as herpes labialis and herpes encephalitis accompanied by HSV-1 infection and genital herpes accompanied by HSV-2, so that it is useful as an general-purpose anti-herpesvirus agent.

Pharmacological actions of the compound of the invention were confirmed by the following pharmacological tests.

TEST EXAMPLE 1 ANTI-VZV ACTIVITY ASSAY

This assay was carried out in accordance with the method described by Shigeta S. (*The Journal of Infectious Diseases*, 147, 3, 576–584 (1983). Illustratively, HEF cells were seeded a 96 well microtiter plate at 10,000 cells per well using a propagation medium and cultured at 37° C. for 4 days in an atmosphere of 5% $CO_2$ until monolayers were formed. After washing the cells with a maintaining medium, the cells were inoculated with 100 µl/well of VZV (strain CaQu) which had been diluted to 20 to 30 pfu/100 μl with the maintaining medium. The plate was centrifuged at 2,000 rpm for 20 minutes at room temperature and then incubated at 37° C. for 3 hours in an atmosphere of 5% $CO_2$ to infect with VZV. After washing three times with 100 μl/well of the maintaining medium, 100 μl of each test drug diluted to an appropriate concentration with the maintaining medium was added to each well. After culturing the cells at 37° C. for 3 to 4 days in an atmosphere of 5% $CO_2$, the cells were fixed with 100 μl/well of 10% formalin/PBS for 2 to 3 hours. After discarding the fixing solution and culture supernatant and subsequently washing the plate with water, a staining solution (0.025% Crystal Violet) was added in 50 μl/well to carry out 2 to 3 minutes for staining, and then the plate was washed with water and dried at 37° C. The HEF cells infected with VZV cause cell death, and plaques comprising dead cells are formed in the monolayer HEF cells. The number of plaques was counted under a microscope, and $EC_{50}$ value of the test drug was calculated as a concentration to inhibit 50% of the plaques.

The $EC_{50}$ values (μM) of the compounds of the invention are shown in the following table. The compounds of the invention were possessed of excellent anti-viral activity against VZV in comparison with acyclovir and known thiazolylphenyl derivatives (Comparative Compounds a and b).

TABLE 1

| Test compound | $EC_{50}$ | Test compound | $EC_{50}$ | Test compound | $EC_{50}$ |
|---|---|---|---|---|---|
| Example 7 | 0.046 | Example 21 | 0.062 | Example 25 | 0.067 |
| Example 32 | 0.094 | Example 39 | 0.042 | Example 40 | 0.038 |
| Example 42 | 0.087 | Example 43 | 0.031 | Example 44 | 0.030 |
| Example 50 | 0.059 | Example 52 | 0.042 | Example 53 | 0.065 |
| Example 54 | 0.034 | Example 55 | 0.055 | Example 56 | 0.041 |
| Example 58 | 0.049 | Example 60 | 0.081 | Example 61 | 0.046 |
| Example 67 | 0.081 | Example 76 | 0.095 | Example 83 | 0.043 |
| Example 85 | 0.090 | Example 104 | 0.12 | Example 105 | 0.52 |
| Example 108 | 0.025 | Example 110 | 0.049 | Example 111 | 0.026 |
| Example 113 | 0.040 | Example 114 | 0.070 | Example 115 | 0.028 |
| Example 116 | 0.033 | Example 117 | 0.065 | Example 118 | 0.059 |
| ACV | 4.3 | Comp. Comp. a | 3.0 | Comp. Comp. b | 1.1 |

ACV: acyclovir

ACV: Acyclovir

Comparative Compounds a and b: compounds of entry Nos. 29 and 34 in Table 1 of WO 97/24343

Comparative Compound a

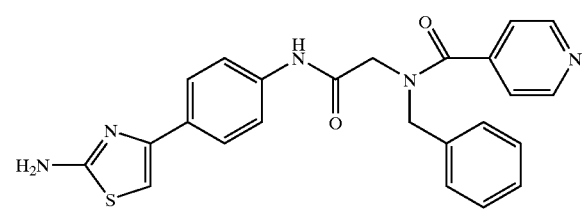

Comparative Compound b

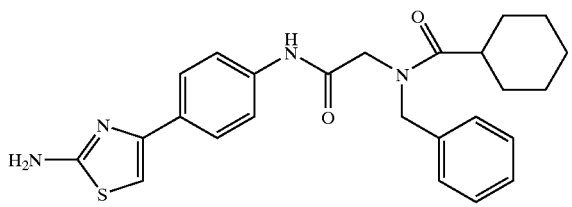

TEST EXAMPLE 2 CUTANEOUS HSV-1 INFECTION MOUSE MODEL (IN VIVO TEST)

Using a cutaneous HSV-1 infection mouse model prepared in accordance with the method of H. Machida et al. (*Antiviral Res.*, 1992, 17, 133–143), in vivo activity of the compounds of the invention was tested. The skin of each HR-1 hairless mouse was scratched lengthwise and breadthwise several times using a needle and a virus suspension (HSV-1 strain WT-51, 1.5×10⁴ PFU) was droped to the scarified region for infection. A compound of the invention (the compound of Example 49 or the compound of Example 87) was made into a methyl cellulose suspension and orally administered at a dose of 25 mg/kg twice a day for 5 days. Symptoms of the skin lesion caused by the HSV-1 infection were scored into 7 degrees and evaluated for 21 days, and survived days of mice were also examined.

As a result, in the placebo group, increase in the score was observed on and after 4th day of the infection due to worsening of the symptoms of the skin lesion, the average lesion score exceeded 6 on the 7th day, and the number of survived days was 10 days or less. On the other hand, in the group in which the compound of the invention was administered, development of skin lesion was inhibited almost completely, and the lesion score was 1 or less during the evaluation period. Also, prolongation of survived days was found and mortal case was not found during the evaluation period.

Thus, it was confirmed that the compound of the invention has also excellent anti-herpesvirus activity in vivo.

The pharmaceutical composition of the invention which contains one or two or more of the compounds represented by the general formula (I) as the active ingredient can be prepared by generally used methods using pharmaceutical carriers, fillers and the like which are generally used in this field. Its administration may be either oral administration by tablets, pills, capsules, granules, powders, solutions and the like, or parenteral administration by intravenous, intramuscular and the like injections, suppositories, eye drops, eye ointments, inhalations and the like.

As the solid composition for oral administration according to the invention, tablets, powders, granules and the like are used. In such a solid composition, one or more active substances are mixed with at least one inert diluent such as lactose, mannitol, glucose, hydroxypropylcellulose, microcrystalline cellulose, starch, polyvinyl pyrrolidone, magnesium aluminate metasilicate or the like. In the usual way, the composition may contain inert additives such as magnesium stearate or the like lubricant, sodium carboxymethylstarch or the like disintegrating agent and solubilization assisting agent. If necessary, tablets or pills may be coated with a sugar or a gastric or enteric coating agent.

The liquid composition for oral administration includes pharmaceutically acceptable emulsions, solutions, suspensions, syrups, elixirs and the like and contains a generally used inert diluent such as purified water or ethyl alcohol. In addition to the inert diluent, this composition may also contain a solubilizing agent, a moistening agent, a suspending agent and the like auxiliary agents, as well as sweeteners, flavors, aromatics and preservatives.

The injections for parenteral administration include sterile aqueous or non-aqueous solutions, suspensions and emulsions. Examples of the aqueous solution include distilled water for injection and physiological saline. Examples of the non-aqueous solution include propylene glycol, polyethylene glycol, olive oil or the like plant oil, ethyl alcohol or the like alcohol, polysorbate 80 (trade name) and the like. Such a composition may further contain a tonicity agent, an antiseptic, a moistening agent, an emulsifying agent, a dispersing agent, a stabilizing agent and a solubilization assisting agent. These are sterilized by, e.g., filtration through a bacteria retaining filter, blending of a germicide or irradiation. Alternatively, they may be used by firstly making into sterile solid compositions and dissolving or suspending them in sterile water or a sterile solvent for injection prior to their use.

In general, daily dose in the case of oral administration is from about 0.001 to 50 mg/kg body weight, preferably from 0.01 to 30 mg/kg, and daily dose in the case of parenteral administration is from about 0.0001 to 10 mg/kg body weight, and the daily dose is divided into 1 to several doses per day. The dosage is optionally decided by taking into consideration symptoms, age, sex and the like in response to each case.

BEST MODE FOR CARRYING OUT THE INVENTION

The following describes the invention further in detail based on examples. The invention is not limited to those described in the following examples. In this connection, production examples of material compounds of the compounds of the invention are shown in Reference Examples.

REFERENCE EXAMPLE 1

Potassium carbonate and ethyl bromoacetate were added to DMF solution of aniline and stirred under heating. After adding water and ethyl acetate to the reaction mixture, the organic layer was separated, washed and dried, and then the solvent was evaporated under a reduced pressure to obtain a crude product. This was dissolved in chloroform, mixed with TEA, 4-fluorobenzoyl chloride and dimethylaminopyridine (DMAP) and stirred. After adding 1 M hydrochloric acid to the reaction solution, the organic layer was separated, washed and dried, and then the solvent was evaporated under a reduced pressure. By purifying the thus obtained crude product by a silica gel column chromatography (to be referred to as SCG hereinafter), ethyl [(4-fluorobenzoyl) phenylamino]acetate (colorless oil) was obtained.

REFERENCE EXAMPLE 2

Potassium carbonate and benzyl bromoacetate were added to DMF solution of ethyl (4-aminophenoxy)acetate and stirred under heating. After adding water and ethyl acetate to the reaction mixture, the organic layer was separated, washed and dried, and then the solvent was evaporated under a reduced pressure. Dichloromethane solution of the thus obtained crude product was mixed with TEA, 4-fluorobenzoyl chloride was added dropwise thereto under ice-cooling and then the reaction solution was stirred. After adding 1 M hydrochloric acid to the reaction solution, the organic layer was separated, washed and dried, and then the solvent was evaporated under a reduced pressure. By purifying the thus obtained crude product by SCG, ethyl {4-[benzyloxycarbonylmethyl-(4-fluorobenzoyl)amino] phenoxy}acetate (colorless oil) was obtained.

REFERENCE EXAMPLE 3

A mixture of 6-aminoquinoline, di-tert-butyl dicarbonate and DMAP was stirred under heating. 1,4-Dioxane and 1 M sodium hydroxide aqueous solution were added the reaction mixture and stirred. Ethyl acetate was added to the reaction solution, the organic layer was separated, washed and dried, and then the solvent was evaporated under a reduced pressure. By purifying the thus obtained crude product by SCG, 6-(tert-butyloxycarbonyl)aminoquinoline was obtained. This was dissolved in ethanol, mixed with 20% palladium hydroxide-carbon and stirred in an atmosphere of hydrogen. After filtering the reaction solution, the solvent was evaporated under a reduced pressure to obtain a tetrahydroquinoline compound. This was dissolved in 1,4-dioxane, mixed with 9H-fluorenyl-9-ylmethyl chloroformate and 10% sodium bicarbonate aqueous solution and then stirred. By adding ethyl acetate and water to the reaction solution, the organic layer was separated, washed and dried, and then the solvent was evaporated under a reduced pressure. The residue was dissolved in chloroform, mixed with trifluoroacetic acid and stirred. The solvent was evaporated under a reduced pressure, the residue was mixed with ethyl acetate, washed and dried, and then the solvent was evaporated under a reduced pressure. By purifying the thus obtained crude product by SCG, 9H-fluorenyl-9-ylmethyl 6-amino-1,2,3,4-tetrahydroquinoline-1-carboxylate was obtained. This was dissolved in acetonitrile, mixed with potassium carbonate and benzoyl bromoacetate and then stirred under heating. The reaction mixture was filtered, and the solvent was evaporated under a reduced pressure. The thus obtained crude product was purified by SCG. This was dissolved in pyridine, mixed with dichloromethane and 4-fluorobenzoyl chloride and then stirred. After adding ethyl acetate and water to the reaction mixture, the organic layer was separated, washed and dried, and then the solvent was evaporated under a reduced pressure. By purifying the thus obtained crude product by SCG, ethyl {[1-(9H-fluorenyl-9-ylmethyloxycarbonyl)-1,2,3,4-tetrahydroquinolin-6-yl](4-fluorobebzoyl)amino}acetate (pale yellow foam) was obtained.

REFERENCE EXAMPLE 4

Potassium carbonate and ethyl bromoacetate were added to DMF solution of 6-amino-1-indanone and stirred under heating. After addition of ethyl acetate to the reaction mixture and subsequent filtration, the organic layer was washed and dried, and then the solvent was evaporated under a reduced pressure to obtain an ester compound. This was dissolved in chloroform, mixed with TEA and 4-fluorobenzoyl chloride and then stirred. Subsequently, the reaction solution was mixed with TEA and 4-fluorobenzoyl chloride and then stirred. After addition of ethyl acetate to the reaction solution and subsequent filtration, the solvent of the mother liquid was evaporated under a reduced pressure. The thus obtained crude product was purified by SCG. This was dissolved in ethanol and stirred by adding sodium borohydride. Subsequently, the reaction solution was mixed with sodium borohydride and methanol and stirred. The reaction solution was mixed with water and chloroform, the organic layer was separated, washed and dried, the solvent was evaporated under a reduced pressure, and then the thus obtained crude product was purified by SCG to obtain ethyl [(4-fluorobenzoyl)(3-hydroxyindan-5-yl)amino]acetate (yellow oil).

REFERENCE EXAMPLE 5

A mixture of 2-chloropyridine and ethyl aminoacetate hydrochloride was stirred under heating. After addition of ethyl acetate and saturated sodium bicarbonate aqueous solution to the reaction mixture and subsequent separation, the organic layer was washed and dried, and the solvent was evaporated under a reduced pressure. The thus obtained crude product was purified by SCG. This was dissolved in dichloromethane and stirred by adding pyridine, 4-fluorobenzoyl chloride and DMAP. The reaction solution was mixed with ethyl acetate and water, the organic layer was separated, washed and dried, and then the solvent was evaporated under a reduced pressure. The thus obtained crude product was purified by SCG to obtain ethyl [(4-fluorobenzoyl)(2-pyridyl)amino]acetate (colorless oil).

REFERENCE EXAMPLE 6

A chloroform solution of ethyl [(4-piperidinecarbonyl)(4-methoxyphenyl)amino]acetate was stirred by adding acetic acid, sodium triacetoxyborohydride and 36% formaldehyde aqueous solution. And furthermore, the reaction solution was stirred by adding sodium triacetoxyborohydride and 36% formaldehyde aqueous solution. The reaction solution was neutralized by adding saturated sodium bicarbonate aqueous solution, the organic layer was separated by adding chloroform, washed and dried, and then the solvent was evaporated under a reduced pressure. The thus obtained crude product was purified by SCG to obtain ethyl {[(1-methyl-4-piperidine)carbonyl](4-methoxyphenyl)amino}acetate (colorless oil).

REFERENCE EXAMPLE 7

Thionyl chloride was added to 1,4-dioxane solution of (1-benzyloxycarbonyl-4-piperidine)carboxylic acid and stirred, and the solvent was evaporated under a reduced pressure. The residue was dissolved in chloroform and stirred by adding ethyl [(4-methoxyphenyl)amino]acetate and TEA, and then the solvent was evaporated under a reduced pressure. The residue was diluted with ethyl acetate, washed and dried, and then the solvent was evaporated under a reduced pressure. The thus obtained crude product was purified by SCG. This was dissolved in ethanol, mixed with 5% Pd—C and then stirred at room temperature in an atmosphere of hydrogen. After filtration of the reaction solution, the solvent was evaporated under a reduced pressure to obtain ethyl [(4-piperidinecarbonyl)(4-methoxyphenyl)amino]acetate. This was dissolved in THF and stirred by adding di-tert-butyl dicarbonate and TEA. The reaction solution was stirred by adding 1 M sodium hydroxide aqueous solution and then stirred by adding 1 M sodium hydroxide aqueous solution and ethanol. The reaction solution was mixed with 1 M hydrochloric acid and extracted with chloroform-ethanol (10/1), the organic layer was dried and then the solvent was evaporated under a reduced pressure to obtain {[(1-tert-butyloxycarbonyl-4-piperidine)carbonyl](4-methoxyphenyl)amino}acetic acid (colorless amorphous).

REFERENCE EXAMPLE 8

A chloroform solution of ethyl [(4-methoxyphenyl)-(tetrahydrothiopyran-4-carbonyl)amino]acetate was stirred by adding 3-chloroperbenzoic acid (>65%; MCPBA). Sodium bicarbonate aqueous solution was added to the reaction mixture, the organic layer was separated, washed and dried, and then the solvent was evaporated under a reduced pressure. By purifying the thus obtained crude product by SCG, ethyl [(4-methoxyphenyl)-(1-oxo-tetrahydrothiopyran-4-carbonyl)amino]acetate (pale brown foam) was obtained.

REFERENCE EXAMPLE 9

A DMF solution of ethyl 4-hydroxycyclohexane carboxylate and 4-chlorobenzyl bromide was mixed with NaH and stirred. The reaction solution was mixed with 10% ammonium chloride and ethyl acetate, the organic layer was separated, washed and dried, and then the solvent was evaporated under a reduced pressure. By purifying the thus obtained crude product by SCG, ethyl 4-cis-(4-chlorobenzyloxy)cyclohexanecarboxylate and then ethyl 4-trans-(4-chlorobenzyloxy)cyclohexanecarboxylate were obtained. An ethanol solution of the latter was mixed with 1 M sodium hydroxide aqueous solution and stirred. After adjusting the reaction solution was acidified with 1 M hydrochloric acid, the organic layer was separated by adding chloroform, washed and dried, and then the solvent was evaporated under a reduced pressure. By washing the thus obtained crude product with diisopropyl ether, 4-trans-(4-chlorobenzyloxy)cyclohexanecarboxylic acid was obtained. A dichloromethane solution of this was mixed with one drop of DMF and oxalyl chloride and stirred. Saturated sodium bicarbonate aqueous solution and chloroform were added to the reaction solution to separate the organic layer. The thus obtained crude product was purified by SCG. Its ethyl acetate solution was mixed with 5% Pd—C and stirred in an atmosphere of hydrogen. The reaction solution was filtered and then the solvent was evaporated under a reduced pressure to obtain [(4-trans-hydroxycyclohexanecarbonyl)(4-methoxyphenyl)amino]acetic acid (colorless solid).

REFERENCE EXAMPLE 10

A chloroform solution of ethyl [(4-methoxyphenyl)-(tetrahydrothiopyran-4-carbonyl)amino]acetate was mixed with MCPBA and stirred. After adding sodium bicarbonate aqueous solution to the reaction mixture, the organic layer was separated, washed and dried, and then the solvent was evaporated under a reduced pressure. By purifying the thus obtained crude product by SCG, ethyl [(4-methoxyphenyl)-(1,1-dioxo-tetrahydrothiopyran-4-carbonyl)amino]acetate (white foam) was obtained.

REFERENCE EXAMPLE 11

A chloroform solution of tert-butyl [4-(4-{2-[(9H-fluoren-9-ylmethoxycarbonyl)-(4-methoxyphenyl)amino]acetylamino}phenyl)thiazol-2-yl]carbamate was mixed with piperidine and stirred. The thus precipitated precipitate was filtered and then washed to obtain tert-butyl (4-{4-[2-(4-methoxyphenylaminoacetylamino)phenyl]thiazol-2-yl}carbamate (white solid).

REFERENCE EXAMPLE 12

An ethanol solution of ethyl [(4-fluorobenzoyl)-(4-fluorophenyl)amino]acetate was mixed with 3 M sodium hydroxide aqueous solution and heated under reflux. The reaction solution was concentrated, the residue was mixed with 1 M hydrochloric acid and chloroform, the organic layer was separated, washed and dried and then the solvent was evaporated under a reduced pressure. A dichloromethane solution of the thus obtained carboxylic acid crude product was mixed with 4-aminoacetophenone and WSC.HCl in that order and then stirred. The reaction solution was mixed with 1 M hydrochloric acid, the organic layer was separated, washed and dried and then the solvent was evaporated under a reduced pressure. By purifying the thus obtained crude product by SCG, N-[(4-acetyl-phenylcarbamoyl)methyl]-4-fluoro-N-(4-fluorophenyl)benzamide (white foam) was obtained.

REFERENCE EXAMPLE 13

An ethanol solution of methyl N-[(4-acetylphenylcarbamoyl)methyl]-N-(4-fluorophenyl)terephthalamate was mixed with 1 M sodium hydroxide aqueous solution and heated under reflux. The reaction solution was concentrated, 1 M hydrochloric acid and chloroform were added to the residue, the organic layer was separated, washed and dried and then the solvent was evaporated under a reduced pressure. A toluene suspension of the thus obtained carboxylic acid crude product was mixed with thionyl chloride and a small amount of DMF and heated under reflux. After evaporating the solvent under a reduced pressure, the residue was dissolved in dichloromethane, and the solution was mixed with 28% aqueous ammonia under ice-cooling and stirred at the same temperature. The organic layer was separated, washed and dried, and then the solvent was evaporated under a reduced pressure. By purifying the thus obtained crude product by SCG, N-[(4-acetylphenylcarbamoyl)methyl]-N-(4-fluorophenyl)terephthalamide (pale yellow solid) was obtained.

REFERENCE EXAMPLES 14 TO 99

The compounds of Reference Examples 14 to 38, 40 and 42 to 97 shown in Tables 2 to 6 describing later were obtained in the same manner as in Reference Example 1, the compounds of Reference Examples 39 and 41 shown in Table 2 describing later were obtained in the same manner as in Reference Example 2, the compound of Reference Example 98 shown in Table 6 describing later were obtained in the same manner as in Reference Example 4, and the compounds of Reference Examples 99 and 100 shown in Table 7 describing later were obtained in the same manner as in Reference Example 12.

EXAMPLE 1

Ethanol (10 ml) solution of ethyl [(4-fluorobenzoyl)phenylamino]acetate (599 mg) was mixed with 1 M sodium hydroxide aqueous solution (2.3 ml) and then stirred at room temperature for 5 hours. After changing liquid property of the reaction solution to acidic by adding 1 M hydrochloric acid, water and chloroform were added thereto and the organic layer was separated. Subsequently, the organic layer was dried with anhydrous sodium sulfate and filtered, and then the solvent was evaporated under a reduced pressure. After dissolving the thus obtained crude carboxylic acid in DMF (15 ml), 4-(4-aminophenyl)thiazol-2-ylamine dihydroiodide (831 mg), pyridine (0.23 ml), HOBt (0.3 g) and WSC.HCl (0.42 g) were added thereto in that order and stirred at room temperature for 22 hours. After adding 1 M sodium hydroxide aqueous solution and ethyl acetate to the reaction solution, the organic layer was separated. Subsequently, the organic layer was washed with saturated brine, dried with anhydrous sodium sulfate and filtered, and then the solvent was evaporated under a reduced pressure. The thus obtained crude product was purified by SCG (chloroform/methanol=97/3) to obtain 451 mg of yellow foam. This was dissolved in chloroform-methanol (4 ml-1 ml) and mixed with 4 M hydrogen chloride in ethyl acetate (0.38 ml), and then the solvent was evaporated under a reduced pressure. By recrystallizing the thus obtained crude crystals from ethanol, 270 mg of N-({[4-(2-aminothiazol-4-yl)phenyl]carbamoyl}methyl)-4-fluoro-N-phenylbenzamide monohydrochloride (pale yellow crystals) was obtained.

EXAMPLE 2

Ethanol-chloroform (20 ml-10 ml) solution of N-({[4-(2-aminothiazol-4-yl)phenyl]carbamoyl}methyl)-4-fluoro-N-(4-methanesulfanylphenyl)benzamide (445 mg) was mixed with MCPBA (0.35 g) and then stirred at room temperature for 1 hour. The reaction solution was mixed with saturated sodium bicarbonate aqueous solution (40 ml) and chloroform (10 ml) and then stirred at room temperature for 5 hours. After adding chloroform to the reaction solution, the organic layer was separated, dried with anhydrous sodium sulfate and filtered, and then the solvent was evaporated under a reduced pressure. The thus obtained crude product was purified by SCG (chloroform/methanol=95/5) to obtain 217 mg of a yellow oily substance. This was dissolved in chloroform-methanol (3 ml-3 ml) and mixed with 4 M hydrogen chloride in ethyl acetate (0.35 ml), and then the solvent was evaporated under a reduced pressure. By washing the thus obtained crude product with ethyl acetate, 80 mg of N-({[4-(2-aminothiazol-4-yl)phenyl]carbamoyl}methyl)-4-fluoro-N-(4-methanesulfinylphenyl)benzamide monohydrochloride (pale yellow foam) was obtained.

EXAMPLE 3

Ethyl ether (50 ml) solution of ethyl 4-[ethoxycarbonylmethyl(4-fluorobenzoyl)amino]benzoate (700 mg) was mixed with potassium trimethylsilanolate (0.29 g, 90%) and then stirred at room temperature for 24 hours. After collecting the precipitate by filtration and dissolving in water, liquid property of the solution was changed to acidic by adding 1 M hydrochloric acid, and the organic layer was separated by adding chloroform. Subsequently, the organic layer was dried with anhydrous sodium sulfate and filtered, and then the solvent was evaporated under a reduced pressure. After dissolving the thus obtained crude carboxylic acid in DMF (10 ml), 4-(4-aminophenyl)thiazol-2-ylamine dihydroiodide (358 mg), pyridine (0.09 ml), HOBt (0.16 g) and WSC.HCl (0.23 g) were added thereto in that order and stirred at room temperature for 3 days. After adding saturated sodium bicarbonate aqueous solution and ethyl acetate to the reaction solution, the organic layer was separated. Subsequently, the organic layer was washed with saturated brine, dried with anhydrous sodium sulfate and filtered, and then the solvent was evaporated under a reduced pressure. The thus obtained crude product was purified by SCG (chloroform/methanol=98/2) to obtain 130 mg of a colorless foam. A chloroform-ethanol (2 ml-2 ml) solution of this compound (62 mg) was mixed with 4 M hydrogen chloride in ethyl acetate (0.1 ml), and then the solvent was evaporated under a reduced pressure. By washing the thus obtained crude product with ethyl acetate, 42 mg of N-[({[4-(2-aminothiazol-4-yl)phenyl]carbamoyl}methyl)-(4-fluorobenzoyl)amino]benzoate monohydrochloride (amorphous solid) was obtained.

EXAMPLE 4

Ethanol (100 ml) solution of ethyl {4-[benzyloxycarbonylmethyl-(4-fluorobenzoyl)amino]

phenoxy}acetate (6.4 g) was mixed with 10% Pd—C (500 mg) and then stirred at room temperature overnight in an atmosphere of hydrogen. After filtering the reaction mixture by celite, the filtrate was concentrated. After dissolving the thus obtained crude carboxylic acid in DMF (80 ml), 4-(4-aminophenyl)thiazol-2-ylamine dihydroiodide (5.5 g), pyridine (1.8 ml), HOBt (2.6 g) and WSC.HCl (3.7 g) were added thereto in that order and stirred at room temperature for 3 hours. After adding 10% potassium carbonate aqueous solution and ethyl acetate to the reaction solution, the organic layer was separated. Subsequently, the organic layer was washed twice with 5% brine, washed with saturated brine, dried with anhydrous magnesium sulfate and filtered, and then the solvent was evaporate under a reduced pressure. The thus obtained crude product was purified by SCG (chloroform/methanol=97/3→95/5) to obtain 2.0 g of yellow foam. A chloroform-ethanol (20 ml-5 ml) solution of this compound (900 mg) was mixed with 4 M hydrogen chloride in ethyl acetate (0.6 ml), and then the solvent was evaporated under a reduced pressure. By recrystallizing the thus obtained crude crystals from ethanol, 540 mg of ethyl {4-N-({[4-(2-aminothiazol-4-yl)phenyl]carbamoyl}methyl)-N-(4-fluorobenzoyl)amino phenoxy}acetate monohydrochloride (white crystals) was obtained.

EXAMPLE 5

Ethanol-THF (50 ml-10 ml) solution of ethyl {[4-(4-tert-butoxycarbonylpiperazin-1-yl)phenyl]-(4-fluorobenzoyl)amino}acetate (2.4 g) was mixed with 1 M sodium hydroxide aqueous solution (9.9 ml) and then stirred under heating at 60° C. for 1 hour. After concentration of the reaction solution, the residue was mixed with 1 M hydrochloric acid and chloroform to separate the organic layer. The organic layer was washed with saturated brine, dried with anhydrous magnesium sulfate and filtered, and then the solvent was evaporated under a reduced pressure. After dissolving the thus obtained crude carboxylic acid in DMF (50 ml), 4-(4-aminophenyl)thiazol-2-ylamine dihydroiodide (1.5), pyridine (0.4 ml), HOBt (580 mg) and WSC.HCl (820 mg) were added thereto in that order and stirred at room temperature for 3 hours. After adding 10% potassium carbonate aqueous solution and ethyl acetate to the reaction solution, the organic layer was separated. Subsequently, the organic layer was washed twice with 5% brine, washed with saturated brine, dried with anhydrous magnesium sulfate and filtered, and then the solvent was evaporated under a reduced pressure. The thus obtained crude product was dissolved in chloroform (30 ml), mixed with trifluoroacetic acid (15 ml) and then stirred at room temperature for 3 hours. After concentration of the reaction solution, 10% potassium carbonate aqueous solution and chloroform were added to the resulting residue, and the organic layer was separated. The organic layer was washed saturated brine, dried with anhydrous magnesium sulfate and filtered, and then the solvent was evaporated under a reduced pressure. The thus obtained crude product was purified by SCG (chloroform/methanol/28% aqueous ammonia=96/4/0.4→92/8/0.8) to obtain 210 mg of yellow foam. This was dissolved in chloroform-ethanol (20 ml-5 ml) and mixed with 4 M hydrogen chloride in ethyl acetate (0.4 ml), and then the solvent was evaporated under a reduced pressure. By recrystallizing the thus obtained crude crystals from ethanol, 170 mg of N-({[4-(2-aminothiazol-4-yl)phenyl]carbamoyl}methyl)-4-fluoro-N-(4-piperazin-1-ylphenyl)benzamide trihydrochloride (white crystals) was obtained.

EXAMPLE 6

Ethanol (30 ml) solution of ethyl {4-[N-({[4-(2-aminothiazol-4-yl)phenyl]carbamoyl}methyl)-N-(4-fluorobenzoyl)amino]phenoxy}acetate (1.3 g) was mixed with 1 M sodium hydroxide aqueous solution (2.4 ml) and then stirred at room temperature overnight. After concentration of the reaction solution, the thus obtained crude product was recrystallized from ethanol to obtain 680 mg of sodium (4-[N-({[4-(2-aminothiazol-4-yl)phenyl]carbamoyl}methyl)-N-(4-fluorobenzoyl)amino]phenoxy)acetate (white crystals).

EXAMPLE 7

Ethanol (50 ml) solution of ethyl {[1-(tert-butyloxycarbonyl)-2,3-dihydro-1H-indol-6-yl](4-fluorobenzoyl)amino}acetate (2.57 g) was mixed with 1 M sodium hydroxide aqueous solution (12 ml) and then stirred at room temperature for 5 hours. The reaction solution was mixed with 1 M hydrochloric acid (12 ml) and extracted with chloroform. The organic layer was dried with anhydrous sodium sulfate and filtered, and then the solvent was evaporated under a reduced pressure. After dissolving the thus obtained carboxylic acid derivative in DMF (100 ml), 4-(4-aminophenyl)thiazol-2-ylamine dihydroiodide (2.24 g), pyridine (0.47 ml), HOBt (0.78 g) and WSC.HCl (1.1 g) were added thereto in that order and stirred at room temperature for 18 hours. After adding 1 M sodium hydroxide aqueous solution and ethyl acetate to the reaction solution, the organic layer was separated. Subsequently, the organic layer was washed with saturated brine, dried with anhydrous sodium sulfate and filtered, and then the solvent was evaporated under a reduced pressure. The thus obtained crude product was purified by SCG (chloroform/methanol=98/2) to obtain N-({[4-(2-aminothiazol-4-yl)phenyl]carbamoyl}methyl)-4-fluoro-N-[1-(tert-butyloxycarbonyl)-2,3-dihydro-1H-indol-6-yl]benzamide. This was dissolved in chloroform (20 ml), mixed with trifluoroacetic acid and stirred at room temperature for 20 minutes. The residue was diluted with ethyl acetate and washed with 1 M sodium hydroxide aqueous solution, the organic layer was dried with anhydrous sodium sulfate and filtered, and then the solvent was evaporated under a reduced pressure. The thus obtained crude product was washed with ethyl acetate/hexane/ethanol (12/4/1) to obtain 966 mg of a pale brown solid. Chloroform-ethanol (1/1) solution of this solid matter (398 mg) was mixed with 4 M hydrogen chloride in ethyl acetate (1 ml) and then the solvent was evaporated under a reduced pressure. By washing the thus obtained residue with isopropyl alcohol, 283 mg of N-({[4-(2-aminothiazol-4-yl)phenyl]carbamoyl}methyl)-4-fluoro-N-(2,3-dihydro-1H-indol-6-yl)benzamide dihydrochloride (pale brown amorphous solid) was obtained.

EXAMPLE 8

Ethyl acetate (70 ml) solution of ethyl {[1-(9H-fluorenyl-9-ylmethyloxycarbonyl)-1,2,3,4-tetrahydroquinolin-6-yl](4-fluorobenzoyl)amino)acetate (2.21 g) was mixed with 5% Pd—C (0.22 g) and then stirred at room temperature for 3 hours in an atmosphere of hydrogen. The reaction solution was filtered through celite and then the solvent was evaporated under a reduced pressure. The thus obtained carboxylic acid derivative was dissolved in DMF (50 ml), and 4-(4-aminophenyl)thiazol-2-ylamine dihydroiodide (1.34 g), pyridine (0.27 ml), HOBt (0.47 g) and WSC.HCl (0.67 g) were added thereto in that order and stirred at room temperature for 5 hours. After adding saturated sodium bicarbonate aqueous solution and ethyl acetate to the reaction solution, the organic layer was separated. The organic layer was dried with anhydrous sodium sulfate and filtered, and then the solvent was evaporated under a reduced pressure. The thus obtained crude product was purified by SCG (chloroform/methanol=98.5/1.5) to obtain N-({[4-(2-aminothiazol-4-yl)phenyl]carbamoyl}methyl)-4-fluoro-N-

[1-(9H-fluorenyl-9-ylmethyloxycarbonyl)-1,2,3,4-tetrahydroquinolin-6-yl]benzamide. This was dissolved in pyrrolidine (12 ml) and stirred at room temperature 2.5 hours. The solvent of the reaction solution was evaporated under a reduced pressure, and the residue was purified by SCG (chloroform/methanol=98/2) and washed with chloroform-ethyl acetate-hexane-ethanol (24/12/12/1) to obtain a colorless solid. Chloroform-ethanol (4 ml-4 ml) solution of this solid matter (277 mg) was mixed with 4 M hydrogen chloride in ethyl acetate (0.5 ml) and then the solvent was evaporated under a reduced pressure. By recrystallizing the thus obtained crude crystals from isopropyl alcohol, 229 mg of N-({[4-(2-aminothiazol-4-yl)phenyl]carbamoyl}methyl)-4-fluoro-N-(1,2,3,4-tetrahydroquinolin-6-yl)benzamide dihydrochloride (pale yellow crystals) was obtained.

EXAMPLE 9

A DMF (30 ml) solution of isonicotinic acid (0.12 g) was mixed with CDI (0.16 g) and stirred at room temperature for 10 minutes. A DMF (50 ml) solution of N-({[4-(2-aminothiazol-4-yl)phenyl]carbamoyl}methyl)-4-fluoro-N-(1,2,3,4-tetrahydroquinolin-7-yl)benzamide dihydrochloride (390 mg) was added to the reaction solution at 0° C., and the mixture was gradually warmed to room temperature spending 1 hour while stirring and then stirred at room temperature for 1.5 hours. The reaction solution was mixed with ethyl acetate and washed with a saturated sodium bicarbonate aqueous solution (50 ml)-0.16 M sodium hydroxide aqueous solution (50 ml) mixed solution and then with saturated brine. The organic layer was dried with anhydrous sodium sulfate and filtered, and then the solvent was evaporated under a reduced pressure. The thus obtained crude product was purified by SCG (chloroform/methanol=95/5) to obtain 293 mg of colorless foam. This was dissolved in chloroform-methanol (10 ml-10 ml), mixed with 4 M hydrogen chloride in ethyl acetate (1 ml) and then the solvent was evaporated under a reduced pressure. By recrystallizing the thus obtained crude crystals from isopropyl alcohol, 253 mg of N-({[4-(2-aminothiazol-4-yl)phenyl]carbamoyl}methyl)-4-fluoro-N-[2-(pyridine-4-carbonyl)-1,2,3,4-tetrahydroisoquinolin-7-yl]benzamide dihydrochloride (pale yellow crystals) was obtained.

EXAMPLE 10

THF (40 ml) solution of N-[(4-acetylphenylcarbamoyl)methyl]-N-(4-fluorobenzoyl)terephtalamide (1.1 g) was mixed with phenyltrimethylammonium tribromide (1.1 g) and then stirred at room temperature for 2 hours. The thus formed precipitate was filtered, and the residue obtained by concentrating the resulting filtrate was dissolved in ethanol-THF (20 ml-10 ml), mixed with thiourea (200 mg) and heated under reflux for 3 hours. After concentration of the reaction solution, 5% potassium carbonate aqueous solution and chloroform were added to the resulting residue to separate the organic layer. The organic layer was washed with saturated brine, dried with anhydrous magnesium sulfate and filtered, and then the solvent was evaporated under a reduced pressure. The thus obtained crude product was purified by SCG (chloroform/methanol28% aqueous ammonia=90/101→85/15/1.5) to obtain 380 mg of a pale yellow amorphous solid. By subjecting this to a salt forming reaction using 4 M hydrogen chloride in ethyl acetate, 220 mg of N-({[4-(2-aminothiazol-4-yl)phenyl]carbamoyl}methyl)-N-(4-methoxyphenyl)terephthalamide monohydrochloride (pale yellow amorphous solid) was obtained.

EXAMPLE 11

Methanol (20 ml) solution of methyl N-({[4-(2-aminothiazol-4-yl)phenyl]carbamoyl}methyl)-N-(4-methoxyphenyl)terephthalamate monohydrochloride (800 mg) was mixed with 1 M sodium hydroxide aqueous solution (1.5 ml) and then heated under reflux for 4 hours. The reaction solution was concentrated, and ethanol (20 ml) and diisopropyl ether (10 ml) were added to the thus obtained residue to effect precipitation of crystals. After filtration, the crystals were washed with diisopropyl ether to obtain 530 mg of sodium N-({[4-(2-aminothiazol-4-yl)phenyl]carbamoyl}methyl)-N-(4-methoxyphenyl)terephthalamate (white crystals).

EXAMPLE 12

DMF (20 ml) solution of N-({[4-(2-aminothiazol-4-yl)phenyl]carbamoyl}methyl)-4-methoxymethoxy-N-(4-methoxyphenyl)benzamide (1.1 g) was mixed with 6 M hydrochloric acid (2 ml) and then stirred at room temperature for 3 hours. After adding 10% potassium carbonate aqueous solution and ethyl acetate to the reaction solution, the organic layer was separated. Subsequently, the organic layer was washed twice with 5% brine and then with saturated brine, dried with anhydrous magnesium sulfate and filtered, and then the solvent was evaporated under a reduced pressure. The thus obtained crude product was purified by SCG (chloroform/methanol=97/3→95/5) to obtain 630 mg of white crystals. A chloroform-ethanol (20 ml-5 ml) solution of the crystals was mixed with 4 M hydrogen chloride in ethyl acetate (0.5 ml), and then the solvent was evaporated under a reduced pressure. By recrystallizing the thus obtained crude crystals from ethanol, 470 mg of N-({[4-(2-aminothiazol-4-yl)phenyl]carbamoyl}methyl)-4-hydroxy-N-(4-methoxyphenyl)benzamide monohydrochloride (white crystals) was obtained.

EXAMPLE 13

DMF (50 ml) solution of {[(1-tert-butyloxycarbonyl-4-piperidine)carbonyl](4-methoxyphenyl)amino}acetic acid (1.20 g) was mixed with 4-(4-aminophenyl)thiazol-2-ylamine dihydroiodide (1.03 g), pyridine (0.20 ml), HOBt (0.39 g) and WSC.HCl (0.58 g) in that order and stirred at room temperature for 3 days. After adding ethyl acetate and 1 M sodium hydroxide aqueous solution to the reaction solution, the organic layer was separated. The organic layer was washed with saturated brine, dried with anhydrous sodium sulfate and filtered, and then the solvent was evaporated under a reduced pressure. The thus obtained crude product was purified by SCG (chloroform/methanol=98.5/1.5). A chloroform (20 ml) solution of the thus obtained amide derivative was mixed with trifluoroacetic acid (20 ml) and stirred at room temperature for 10 minutes, and then the solvent was evaporated under a reduced pressure. The residue was dissolved in ethyl acetate and washed with 1 M sodium hydroxide aqueous solution. The precipitate formed during the washing was dissolved in chloroform-methanol (9/1) and then washed with water. The organic layers were combined, dried with anhydrous sodium sulfate and filtered, and then the solvent was evaporated under a reduced pressure. The thus obtained crude product was recrystallized from ethanol-ethyl acetate to obtain 160 mg of colorless crystals. The crystals were dissolved in chloroform-ethanol (20 ml-20 ml) and mixed with 4 M-hydrogen chloride in ethyl acetate (0.3 ml), and then the solvent was evaporated under a reduced pressure. The thus obtained foamy matter was redissolved in ethanol and then concentrated, thereby obtaining 150 mg of N-({[4-(2-aminothiazol-4-yl)phenyl]carbamoyl}methyl)-N-(4-methoxyphenyl)-4-piperidinecarboxamide dihydrochloride (pale yellow foam).

EXAMPLE 14

THF (40 ml) solution of N-[(4-acetylphenylcarbamoyl)methyl]-4-fluoro-N-(4-fluorophenyl)benzamide (2.0 g) was mixed with phenyltrimethylammonium tribromide (2.4 g) and then stirred at room temperature for 2 hours. The thus formed precipitate was filtered, and the residue obtained by concentrating the filtrate was dissolved in ethanol (40 ml), mixed with thioacetamide (480 mg) and then heated under reflux for 1 hour. After concentration of the reaction solution, 1 M sodium hydroxide aqueous solution and chloroform were added to the residue, and the organic layer was separated. The organic layer was washed with saturated brine, dried with anhydrous magnesium sulfate and filtered, and then the solvent was evaporated under a reduced pressure. The thus obtained crude product was purified by SCG (hexane/ethyl acetate=2/3) to obtain 1.1 g of 4-fluoro-N-(4-fluorophenyl)-N-({[4-(2-methylthiazol-4-yl)phenyl]carbamoyl}methyl)benzamide (white crystals).

EXAMPLE 15

Chloroform (20 ml) solution of N-({[4-(2-aminothiazol-4-yl)phenyl]carbamoyl}methyl)-N-(1,3-benzodioxazol-5-yl)-4-fluorobenzamide (480 mg) was mixed with pyridine (0.32 ml) and acetic anhydride (0.28 ml) and then stirred at room temperature for 14 hours. The reaction solution was further mixed with pyridine (0.32 ml), acetic anhydride (0.28 ml) and DMAP (5 mg) and then stirred at room temperature for 2 hours. After evaporation of the solvent of the reaction solution under a reduced pressure, the residue was dissolved in ethyl acetate and washed with 1 M hydrochloric acid, water, 1 M sodium hydroxide aqueous solution, water, saturated sodium bicarbonate aqueous solution and saturated brine in that order. The organic layer was dried with anhydrous sodium sulfate and filtered, and then the solvent was evaporated under a reduced pressure. By washing the thus obtained crude product with chloroform-methanol (1/1) and then with ethanol, 190 mg of N-({[4-(2-acetylaminothiazol-4-yl)phenyl]carbamoyl}methyl)-N-(1,3-benzodioxol-5-yl)-4-fluorobenzamide (colorless solid) was obtained.

EXAMPLE 16

A DMF (10 ml) solution of N-({[4-(2-aminothiazol-4-yl)phenyl]carbamoyl}methyl)-N-(1,3-benzodioxazol-5-yl)-4-fluorobenzamide (750 mg) and N-(tert-butoxycarbonyl)glycine (0.35 g) was mixed with HOBt (0.27 g) and WSC.HCl (0.38 g) in that order and stirred at room temperature for 55 hours. After adding ethyl acetate and water to the reaction solution, the organic layer was separated. Subsequently, the organic layer was washed with saturated brine, dried with anhydrous sodium sulfate and filtered, and then the solvent was evaporated under a reduced pressure. The thus obtained crude product was purified by SCG (hexane/ethyl acetate=60/40→40/60) to obtain 670 mg of tert-butyl ({[4-(4-{2-[(1,3-benzodioxazol-5-yl)-(4-fluorobenzoyl)amino]acetylamino}phenyl)thiazol-2-yl]carbamoyl}methyl)carbamate (yellow foam). This compound (640 mg) was dissolved in trifluoroacetic acid-chloroform (8 ml-8 ml) and stirred at room temperature for 10 minutes. After evaporating solvent of the reaction solution under a reduced pressure, the residue was dissolved in chloroform-methanol (10/1) and washed with 0.1 M sodium hydroxide aqueous solution and water in that order. Subsequently, the organic layer was dried with anhydrous sodium sulfate and filtered, and then the solvent was evaporated under a reduced pressure. The thus obtained crude product was purified by SCG (chloroform/methanol=98/2) to obtain 330 mg of pale yellow foam. This was dissolved in chloroform-methanol (8 ml-9 ml) and mixed with 4 M hydrogen chloride in ethyl acetate (0.45 ml), and then the solvent was evaporated under a reduced pressure. By recrystallizing the thus obtained crude crystals from methanol, 196 mg of N-[({4-[2-(2-aminoacetylamino)thiazol-4-yl]phenyl}carbamoyl)methyl]-N-(1,3-benzodioxol-5-yl)-4-fluorobenzamide monohydrochloride (colorless crystals) was obtained.

EXAMPLE 17

N-{[4-(2-aminothiazol-4-yl)phenylcarbamoyl]methyl}-4-fluoro-N-(4-fluorophenyl)benzamide monohydrochloride (200 mg) was dissolved in a mixed solvent of acetic acid (10 ml) and water (5 ml), mixed with bromine (20 µl) under ice-cooling and then stirred at room temperature for 5 minutes. The reaction solution was concentrated under a reduced pressure, and the residue was dissolved in ethyl acetate (30 ml)-saturated sodium bicarbonate aqueous solution (20 ml). The organic layer was washed with saturated brine, dried with anhydrous sodium sulfate and then concentrated under a reduced pressure. The residue was dissolved in ethyl acetate (5 ml) and mixed with 4 M hydrogen chloride in ethyl acetate solution (0.15 ml), and the thus precipitated solid was collected by filtration, dried and then recrystallized from methanol-ether, thereby obtaining 184 mg of N-{[4-(2-amino-5-bromothiazol-4-yl)phenylcarbamoyl]methyl}-4-fluoro-N-(4-fluorophenyl)benzamide monohydrochloride (colorless powder).

EXAMPLE 18

A methanol-chloroform (40 ml-20 ml) solution of N-({[4-(2-aminothiazol-4-yl)phenyl]carbamoyl}methyl)-N-benzothiazol-6-yl-4-oxocyclohexanecarboxyamide (430 mg) was mixed with sodium borohydride (0.19 g) at 0° C. and then stirred at room temperature for 1 hour. The reaction solution was mixed with water and extracted with chloroform, the organic layer was dried with anhydrous sodium sulfate and filtered, and then the solvent was evaporated under a reduced pressure. The thus obtained crude product was purified by SCG (chloroform/methanol/27% aqueous ammonia=94.8/5/0.2). This was dissolved in chloroform-methanol (10 ml-10 ml) and mixed with 4 M hydrogen chloride in ethyl acetate (1 ml), and then the solvent was evaporated under a reduced pressure. By recrystallizing the thus obtained crude crystals from isopropyl alcohol-ethyl acetate (3/1), 259 mg of N-({[4-(2-aminothiazol-4-yl)phenyl]carbamoyl}methyl)-N-benzothiazol-6-yl-4-hydroxycyclohexanecarboxyamide monohydrochloride (pale yellow crystals) was obtained.

EXAMPLES 19 TO 121

The compounds of Examples 19 to 46, 49 to 62, 64 to 103 and 105 to 121 shown in the following Tables 8 to 18 were obtained in the same manner as in Example 1. Also, the compounds of Examples 47 and 48 were obtained in the same manner as in Example 4, and the compound of Example 63 in the same manner as in Example 7, and the compound of Example 104 in the same manner as in Example 16.

EXAMPLE 121

<Synthesis by Combinatorial Chemistry General Synthesis Method>

A pyridine (1.0 ml) solution of tert-butyl (4-(4-[2-(4-methoxyphenylaminoacetylamino)phenyl]thiazol-2-yl)carbamate (13.8 mg, 30 µmol) was mixed with from 40 to 90 µmol of each of various carbonyl chlorides or sulfonyl chlorides and stirred at a temperature of from room temperature to 70° C. for a period of from 1 hour to 12 hours. By adding 30 to 50 mg of PS-Tris Amine (a scavenger resin mfd. by Argonote, carrying amount 3.0 to 5.0 mmol/g) and stirring at room temperature for 2 to 5 hours, excess amounts of carbonyl chloride or sulfonyl chloride and chloride ions were captured. The PS-Tris Amine was removed by filtration, and pyridine was evaporated under a reduced pressure from the filtered solution. From 10 to 50 mg of respective N-({[4-(2-tert-butoxycarbonylaminothiazol-4-yl)phenyl]carbamoyl}methyl)-N-(4-methoxyphenyl)amide or sulfonamide derivatives hardly containing pyridine salt were obtained.

Each of them was mixed with 0.5 to 2 ml of 4 M hydrogen chloride in ethyl acetate or 50% trifluoroacetic acid in methylene chloride and stirred at a temperature of from ice-cooling to room temperature for a period of from 1 to 4 hours. By evaporating the solvent, from 10 to 50 mg of respective N-({[4-(2-aminothiazol-4-yl)phenyl]carbamoyl}methyl)-N-(4-methoxyphenyl)amide or sulfonamide derivatives were obtained as hydrochloride or trifluoroacetate.

Their purity was verified by a high performance liquid chromatography, and products having low purity were subjected to a high performance liquid chromatography (methanol/5 mM trifluoroacetic acid aqueous solution). At the time of elution from the column, mass spectrometry was simultaneously carried out and only the eluates containing compounds having desired molecular weights were collected. After evaporating the solvent, compounds of interest having improved purity were obtained.

<Synthesis Examples of Compounds: a-1>

A pyridine (1.0 ml) solution of tert-butyl (4-{4-[2-(4-methoxyphenylaminoacetylamino)phenyl]thiazol-2-yl}carbamate (13.8 mg) was mixed with o-toluoyl chloride (10 μl) and stirred at 60° C. for 1.5 hours. By adding 33 mg of PS-Tris Amine (carrying amount 4.61 mmol/g) and stirring at room temperature for 3 hours, excess amounts of o-toluoyl chloride and chloride ions were captured. The PS-Tris Amine was removed by filtration, and pyridine was evaporated under a reduced pressure from the filtered solution. A 16.4 mg portion of N-({[4-(2-tert-butoxycarbonylaminothiazol-4-yl)phenyl]carbamoyl}methyl)-N-(4-methoxyphenyl)-4-methylbenzamide hardly containing pyridine salt was obtained. This was mixed with 4 M hydrogen chloride in ethyl acetate (1.0 ml) and stirred at room temperature for 2.5 hours. By evaporating the solvent, 17.5 mg of N-({[4-(2-aminothiazol-4-yl)phenyl]carbamoyl}methyl)-N-(4-methoxyphenyl)-4-methylbenzamide hydrochloride was obtained.

In the same manner, the compounds of a-2 to a-28 shown in the flowing Table 19 and the compounds of b-1 to b-70 shown in the flowing Tables 20 and 21 were obtained as hydrochloride or trifluoroacetate.

Physicochemical properties of the reference example compounds are shown in Tables 2 to 7, and structures and physicochemical properties of the Example compounds in Tables 8 to 21. Also, other compounds to be included in the invention are illustratively shown in Tables 22 to 25. These compounds can be easily produced in the same manner as the methods described in the aforementioned examples or the production methods, or by applying thereto slight modifications obvious to those skilled in the art.

Abbreviations in the tables respectively means Ref: Reference Example; Ex: Example; Co: compound number; Str: structural formula; Sal: salt; Dat: physicochemical properties {F: FAB-MS (M$^+$); F+: FAB-MS [(M+H)$^+$]; F−: FAB-MS [(M−H)$^-$]; A+: APCI (atmosphere chemical ionization)-MS [(M+H)$^+$]; E+: ESI (electrospray ionization)-MS [(M+H)$^+$]; N1: characteristic peak δ ppm of $^1$H-NMR (DMSO-d$_6$, TMS internal standard); N2: characteristic peak δ ppm of $^1$H-NMR (CDCl$_3$, TMS internal standard)}; Ph: phenyl; Pr: n-propyl; iPr: isopropyl; Ac: acetyl; Bn: benzyl; tBu: tert-butyl; iBu: isobutyl; Bu: n-butyl; cBu: cyclobutyl; Py2: 2-pyridyl; Py3: 3-pyridyl; Py4: 4-pyridyl; Th2: 2-thienyl; Th3: 3-thienyl; Fu: 2-furyl; Pyr: 2-pyrazinyl; Naph1: 1-naphthyl; Naph2: 2-naphthyl; cPen: cyclopentyl; cHex: cyclohexyl; Hep4: 4-heptyl; Pipe: 4-piperidinyl; Pyrr: 2-pyrrolyl; Pyra: 3-pyrazolyl; Ind3: 3-indolyl; and Ind5: 5-indolyl. In this connection, the numeral before each substituent group indicates its substitution position, for example, 3,4-C$_{12}$-5-F-Ph indicates 3,4-dichloro-5-fluorophenyl group.

TABLE 2

(IIIa)

| Ref | A | R | Dat | Ref | A | R | Dat |
|-----|---|---|-----|-----|---|---|-----|
| 1 | Ph | Et | F+: 302 | 2 | 4-Me-Ph-OCH$_2$-CO$_2$Et | Bn | F+: 466 |
| 3 | 6-Me-3,4-dihydroquinolin-1-yl (Fmoc) | Bn | F+: 640 | 4 | 5-Me-indan-1-ol | Et | F+: 358 |

TABLE 2-continued (IIIa)

| Ref | A | R | Dat | Ref | A | R | Dat |
|---|---|---|---|---|---|---|---|
| 5 | Py2 | Et | F+: 303 | 14 | Th3 | Et | F+: 308 |
| 15 | 4-F-Ph | Et | F+: 320 | 16 | 4-Cl-Ph | Et | F+: 336 |
| 17 | 4-Br-Ph | Et | F+: 380 | 18 | 2-F-Ph | Et | F+: 320 |
| 19 | 3-F-Ph | Et | F+: 320 | 20 | 3,4-F$_2$-Ph | Et | F+: 338 |
| 21 | 4-SMe-Ph | Et | F+: 348 | 22 | 4-CO$_2$Et-Ph | Et | F+: 374 |
| 23 | 4-Me-Ph | Et | F+: 316 | 24 | 4-CF$_3$-Ph | Et | F+: 370 |
| 25 | 4-Et-Ph | Et | F+: 330 | 26 | 4-N(Me)$_2$-Ph | H | F+: 317 |
| 27 | 2-OMe-Ph | Et | F+: 332 | 28 | 3-OMe-Ph | Et | F+: 332 |
| 29 | 4-OMe-Ph | Et | F+: 332 | 30 | 3,4-(OMe)$_2$-Ph | Et | F: 361 |
| 31 | 3,4,5-(OMe)$_3$-Ph | Et | F: 391 | 32 | 4-OEt-Ph | Et | F+: 346 |
| 33 | 4-OPr-Ph | Et | F+: 360 | 34 | 4-OiPr-Ph | Et | F+: 360 |
| 35 | 4-OAc-Ph | Et | F+: 360 | 36 | (benzodioxine) | Et | F+: 360 |
| 37 | (methylenedioxyphenyl) | Et | F: 345 | 38 | (4-OCH$_2$CO$_2$Et-Ph) | Bn | F+: 466 |
| 39 | 4-CH$_2$CO$_2$Et-Ph | Bn | F+: 450 | 40 | 4-CH$_2$CN-Ph | Et | F+: 341 |
| 41 | (4-(piperazinyl-CH$_2$CO$_2$Et)-Ph) | Bn | F: 533 | 42 | (4-(piperazinyl-CO$_2$tBu)-Ph) | Et | F+: 485 |
| 43 | (5-methyl-2-methylbenzothiazole) | Et | F+: 373 | 44 | (5-methylbenzothiazole) | Et | F+: 359 |
| 45 | (6-methylbenzothiazole) | Et | F+: 359 | 46 | (4-(2-piperidinylethoxy)-Ph) | Et | F+: 429 |

TABLE 3

| Ref | A | R | Dat | Ref | A | R | Dat |
|---|---|---|---|---|---|---|---|
| 47 | (6-methylindane) | Et | F+: 342 | 48 | (5-methylindole) | Et | F+: 341 |

TABLE 3-continued
| Ref | A | R | Dat | Ref | A | R | Dat |
|---|---|---|---|---|---|---|---|
| 49 | 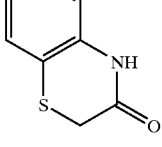 | Et | F+: 389 | 50 | 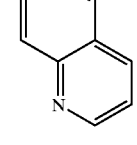 | Et | F+: 353 |
| 51 | 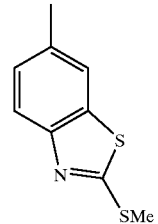 | Et | F+: 405 | 52 | 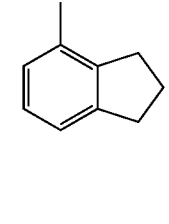 | Et | F+: 342 |
| 53 | 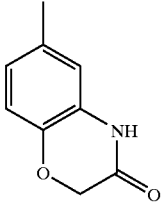 | Et | F+: 373 | 54 | 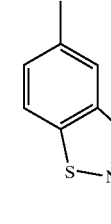 | Et | F+: 359 |
| 55 | 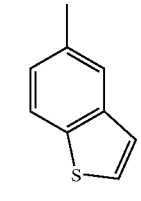 | Et | F+: 358 | 56 | 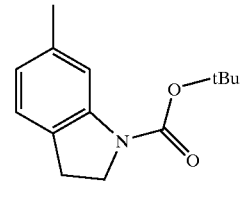 | Et | F+: 443 |
| 57 | 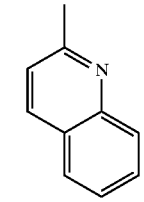 | Et | F+: 353 | 58 | 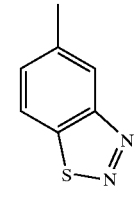 | Et | F+: 360 |
| 59 | 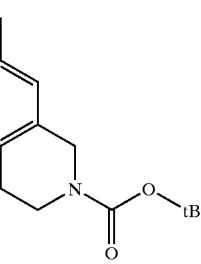 | Et | F+: 457 | | | | |

TABLE 4

| Ref | Str | Dat |
|---|---|---|
| 6 | (structure) | F+: 335 |
| 7 | (structure) | F+: 393 |
| 8 | (structure) | F+: 354 |
| 9 | (structure) | F−: 306 |
| 10 | (structure) | F+: 370 |
| 11 | (structure) | F: 454 |

TABLE 4-continued
| Ref | Str | Dat |
|---|---|---|
| 60 | 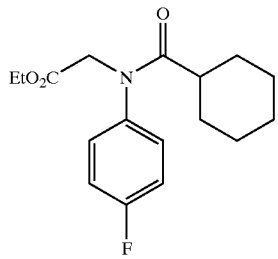 | F+: 308 |
| 61 | 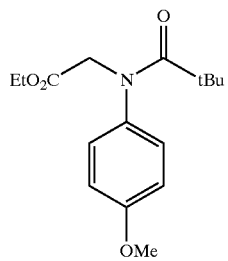 | F+: 294 |
| 62 | 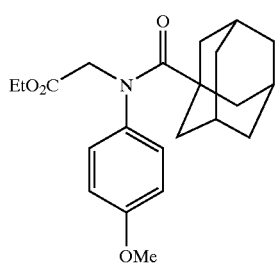 | F−: 370 |
| 63 | 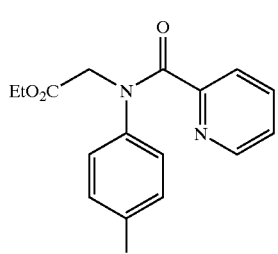 | F+: 315 |
| 64 | 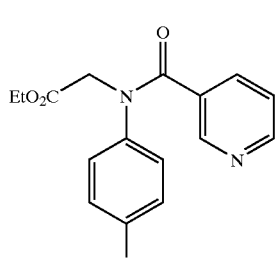 | F+: 315 |

TABLE 4-continued

| Ref | Str | Dat |
|-----|-----|-----|
| 65 | | F+: 315 |
| 66 | | F: 253 |
| 67 | | F: 271 |
| 68 | | F: 493 |
| 69 | | F+: 427 |

TABLE 4-continued

| Ref | Str | Dat |
|-----|-----|-----|
| 70 | (structure) | F+: 347 |
| 71 | (structure) | F+: 349 |

TABLE 5

| Ref | Str | Dat | Ref | Str | Dat |
|-----|-----|-----|-----|-----|-----|
| 72 | (structure) | F: 383 | 73 | (structure) | F+: 342 |
| 74 | (structure) | F+: 342 | 75 | (structure) | F−: 331 |
| 76 | (structure) | F+: 322 | 77 | (structure) | F+: 322 |

TABLE 5-continued

| Ref | Str | Dat | Ref | Str | Dat |
| --- | --- | --- | --- | --- | --- |
| 78 | | F+: 322 | 79 | | F+: 370 |
| 80 | | F+: 338 | 81 | | F+: 418 |
| 82 | | F+: 349 | 83 | | F+: 365 |
| 84 | | F+: 397 | 85 | | F+: 445 |
| 86 | | F+: 363 | 87 | | F+: 383 |

TABLE 6

| Ref | Str | Dat | Ref | Str | Dat |
|---|---|---|---|---|---|
| 88 | | F+: 413 | 89 | | F+: 360 |
| 90 | | F+: 343 | 91 | | F+: 374 |
| 92 | | F+: 418 | 93 | | F+: 386 |
| 94 | | F+: 397 | 95 | | F+: 380 |
| 96 | | F+: 398 | 97 | | F+: 308 |

TABLE 6-continued
| Ref | Str | Dat |
|---|---|---|
| 98 | 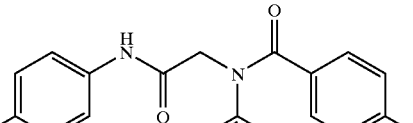 | F+: 398 |
TABLE 7
(XV)
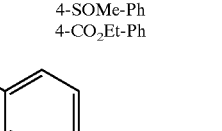
| Ref | $R^2$ | $R^a$ | $R^b$ | Dat | Ref | $R^2$ | $R^a$ | $R^b$ | Dat |
|---|---|---|---|---|---|---|---|---|---|
| 12 | H | F | F | F+: 409 | 13 | H | F | $CONH_2$ | F−: 444 |
| 99 | H | OMe | $CO_2Me$ | F+: 461 | 100 | $CO_2Et$ | F | F | F−: 479 |
TABLE 8
(I)
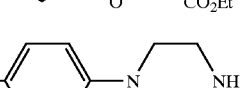
| Ex | A | Sal | Dat |
|---|---|---|---|
| 1 | Ph | HCl | N1: 4.67(2H, s), 7.01–7.40(10H, m), 7.69–7.77 (4H, m),10.50(1H, s) |
| 2 | 4-SOMe-Ph | HCl | F+: 509 |
| 3 | 4-$CO_2$Et-Ph | HCl | F+: 519 |
| 4 | 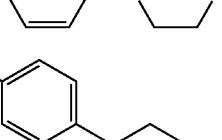 | HCl | N1: 1.17(3H, t), 4.13(2H, q), 4.62(2H, s), 4.72 (2H, s), 6.83(2H, d), 7.08(2H ,m), 7.13(1H, s), 7.17(2H, d), 7.33(2H, m), 7.73(4H, m), 10.5 1(1H, s) |
| 5 | | 3HCl | N1: 3.15(4H, br), 3.32(4H, br), 4.61(2H, s), 6.87(2H, d), 7.07–7.15(5H, m), 7.34(2H, br), 7.74 (4H, br), 10.58(1H, s) |
| 6 | | — | N1: 4.07(2H s), 4.56(2H, s),6.69(2H, d), 6.89 (1H, s), 7.03–7.09(6H, m), 7.33(2H, br), 7.62 (2H d), 7.73(2H, d), 10.52(1H, s) |

TABLE 8-continued

[Structure (I): 2-amino-thiazole connected to phenyl-NH-C(O)-CH2-N(A)-C(O)-phenyl-4-F]

| Ex | A | Sal | Dat |
|---|---|---|---|
| 7 | 6-methyl-indoline (attached at N) | 2HCl | F+: 488<br>N1: 3.08(2H, t), 3.63(2H, t), 4.65(2H, s), 7.06–7.32 (6H, m), 7.33–7.45(2H, m), 7.71–7.79 (4H, m), 10.66(1H, s) |
| 8 | 6-methyl-1,2,3,4-tetrahydroquinoline (attached at N) | 2HCl | F+: 502<br>N1: 1.88(2H, m), 2.68(2H, m), 3.24(2H, m), 4.63 (2H, s), 6.91(1H, m), 6.98(1H, m), 7.10–7.15 (4H, m), 7.39(2H, m), 7,74(4H, br), 10.58(1H, s) |
| 9 | 7-methyl-2-(pyridine-4-carbonyl)-1,2,3,4-tetrahydroisoquinoline | 2HCl | F+: 607 |
| 19 | 4-F-Ph | HCl | F+: 465<br>N1: 4.66(2H, s), 7.07–7.14(5H, m), 7.28–7.36 (4H, m), 7.74(4H, m), 10.55(1H, s) |
| 20 | 4-Cl-Ph | HCl | F+: 481 |
| 21 | 4-Br-Ph | HCl | F+: 527<br>N1: 4.67(2H, s), 7.09–7.21(5H, m), 7.32–7.40 (2H, m), 7.44–7.51(2H, m), 7.69–7.76(4H, m), 10.56(1H, s) |
| 22 | 2-F-Ph | HCl | N1: 4.10–5.17(2H, m), 7.05–7.55(9H, m), 7.69–7.78(4H, m), 10.58(1H, s) |
| 23 | 3-F-Ph | HCl | N1: 4.69(2H, s), 7.00–7.22(6H, m), 7.24–7.44 (3H, m), 7.71–7.78(4H, m), 10.58(1H, s) |

TABLE 9

| Ex | A | Sal | Dat |
|---|---|---|---|
| 24 | 3,4-F$_2$-Ph | HCl | N1: 4.67(2H, s), 7.04–7.18(4H, m), 7.30–7.49 (4H, m), 7.70–7.76(4H, m), 10.56(1H, s) |
| 25 | 4-SMe-Ph | HCl | F+: 493<br>N1: 2.41(3H, s), 4.64(2H, s), 7.07–7.22(7H, m), 7.32–7.40(2H, m), 7.69–7.77(4H, m), 10.54(1H, s) |
| 26 | 4-Me-Ph | HCl | N1: 2.22(3H, s), 4.62(2H, s), 7.04–7.14(7H, m), 7.30–7.38(2H, m), 7.67–7.75(4H, m), 10.39(1H, s) |
| 27 | 4-Et-Ph | HCl | F+: 475 |
| 28 | 4-CF$_3$-Ph | HCl | N1: 4.74(2H, s), 7.09–7.13(3H, m), 7.35–7.45 (4H, m), 7.63–7.76(6H, m), 10.56(1H, s) |
| 29 | 4-N(Me)$_2$-Ph | — | F−: 488 |

TABLE 9-continued

| Ex | A | Sal | Dat |
|---|---|---|---|
| 30 | 2-OMe-Ph | HCl | F+: 477 |
| 31 | 3-OMe-Ph | HCl | F+: 477 |
| 32 | 4-OMe-Ph | HCl | F+: 477<br>N1: 3.69(3H, s), 4.61(2H, s), 6.79–6.86(2H, m), 7.04–7.21(5H, m), 7.28–7.39(2H, m), 7.69–7.75 (4H, m), 10.45(1H, s) |
| 33 | 3,4-(OMe)$_2$-Ph | HCl | F+: 507<br>N1: 3.62(3H, s), 3.68(3H, s), 4.63(2H, s), 6.68–6.83(2H, m), 6.88–6.93(1H, m), 7.05–7.15 (3H, m), 7.30–7.42(2H, m), 7.70–7.77(4H, m), 10.50(1H, s) |
| 34 | 3,4,5-(OMe)$_3$-Ph | HCl | F+: 537 |
| 35 | 4-OEt-Ph | HCl | F+: 491 |
| 36 | 4-OPr-Ph | HCl | F+: 505 |
| 37 | 4-OiPr-Ph | HCl | F+: 505 |
| 38 | 4-OH-Ph | HCl | F+: 463<br>N1: 4.59(2H, s), 6.64(2H, d), 7.03–7.10(4H, m), 7.12(1H, s), 7.30–7.33(2H, m), 7.69–7.75(4H, m), 8.71(1H, brs), 9.55(1H, brs), 10.46(1H,s) |
| 39 | ![benzodioxane] | HCl | F+: 505<br>N1: 4.15–4.21(4H, m), 4.58(2H, s), 6.65–6.76 (2H, m), 6.81(1H, d), 7.07–7.16(3H, m), 7.32–7.42 (2H, m), 7.69–7.75(4H, m), 10.47(1H, s) |
| 40 | ![methylenedioxyphenyl] | HCl | F+: 491<br>N1: 4.59(2H, s), 6.00(2H, s), 6.67–6.82(2H, m), 6.91(1H, d), 7.07–7.17(3H, m), 7.33–7.42(2H, m), 7.68–7.75(4H, m), 10.44(1H, s) |
| 41 | 4-CH$_2$CN-Ph | HCl | F+: 486 |
| 42 | ![2-methylbenzothiazole] | 2HCl | F+: 518<br>N1: 2.76(3H, s), 4.75(2H, s), 7.03–7.11(2H, m), 7.15(1H, s), 7.25–7.32(1H, m), 7.35–7.43(2H, m), 7.70–7.81(5H, m), 7.92(1H, d), 10.59(1H, s) |

TABLE 10

| Ex | A | Sal | Dat |
|---|---|---|---|
| 43 | ![5-benzothiazolyl] | HCl | F+: 504<br>N1: 4.76(2H, s), 7.04–7.12(3H, m), 7.33–7.44 (3H, m), 7.68–7.75(4H, m), 8.00(1H, d), 8.05 (1H, d), 9.40(1H, s), 10.47(1H, s) |
| 44 | ![6-benzothiazolyl] | — | F−: 502<br>N1: 4.73(2H, s), 6.90(1H, s), 7.01–7.12(4H, m), 7.35–7.43(3H, m), 7.59(2H, d), 7.75(2H, d), 7.97(1H, d), 8.10(1H, d), 8.10(1H, d), 9.37(1H, s), 10.26(1H, s) |
| 45 | ![piperidinylethoxyphenyl] | 2HCl | N1: 1.34–1.37(1H, m), 1.65–1.69(1H, m), 1.75–1.84(4H, m), 2.91–3.00(2H, m), 3.39–3.46 4H, m), 4.34(2H, t), 4.62(2H, s), 6.89(2H, d), 7.08(2H, d), 7.12(1H, s), 7.20(2H, d), 7.35 (2H, br), 7.71–7.76(4H, m), 8.74(1H, br), 10.57(2H, br) |
| 46 | Th3 | HCl | N1: 4.60(2H, s), 6.88–7.01(1H, m), 7.09(1H, s), 7.10–7.16(2H, m), 7.22–7.25(1H, m), 7.35–7.44 (3H, m), 7.69–7.73(4H, m), 10.42(1H, s) |
| 47 | 4-CH$_2$COOEt-Ph | HCl | F+: 533 |
| 48 | ![piperazinyl-CO2Et] | 2HCl | N1: 1.25(3H, t), 3.0–3.5(8H, m), 4.24(2H, q), 4.30(2H, s), 4.61(2H, s), 6.88(2H, d), 7.07–7.13 (5H, m) 7.35(2H, m), 7.70–7.76(4H m), 10.55(1H, s) |

TABLE 10-continued
| Ex | A | Sal | Dat |
|---|---|---|---|
| 49 | 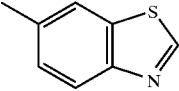 | HCl | F+: 504<br>N1: 4.76(2H, s), 7.07(2H, t), 7.13(1H, s), 7.37–7.42(3H, m), 7.74(4H, brs), 7.97(1H, d), 8.10(1H, d), 9.37(1H, s), 9.37(1H, s), 10.56(1H, s) |
| 50 | 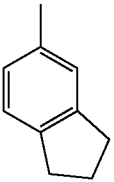 | HCl | F+: 487<br>N1: 1.90–2.02(2H, m), 2.72–2.81(4H, m), 4.63 (2H, s), 6.92(1H, d), 7.05–7.16(5H, m), 7.32–7.41(2H, m), 7.71–7.76(4H, m), 10.53(1H, s) |
| 51 | 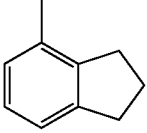 | HCl | F+: 487 |
| 52 | 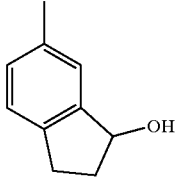 | — | F+: 503<br>N1: 1.66–1.80(1H, m), 2.25–2.36(1H, m), 2.57–2.69(1H, m), 2.76–2.87(1H, m), 4.56(1H, d), 4.63(1H, d), 4.90–4.98(1H, d), 5.26(1H, d), 6.90(1H, s), 6.97–7.13(6H, m), 7.25(1H, br), 7.32–7.43(2H, m), 7.61(2H, d), 7.74(2H, d), 10.20(1H, s) |
TABLE 11
| Ex | A | Sal | Dat |
|---|---|---|---|
| 53 | 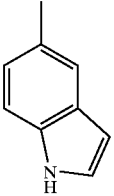 | — | F+: 486<br>N1: 4.63(2H, s), 6.36(1H, s), 6.90(1H, s), 6.96–7.05 (5H, m), 7.26(1H, d), 7.31–7.39(3H, m), 7.44(1H, s), 7.61 (2H, d), 7.74(2H, d), 10.16(1H, s), 11.13(1H, s) |
| 54 | 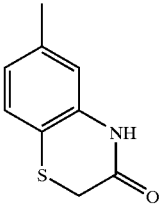 | HCl | F+: 534<br>N1: 3.42(2H, s), 4.61(2H, s), 6.79–6.84(1H, m), 6.89 (1H, d), 7.09–7.24(4H, m), 7.34–7.43(2H, m), 7.68–7.76 (4H, m), 10.48(1H, s), 10.53(1H, s) |
| 55 | 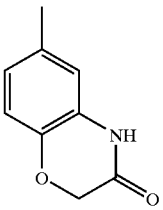 | HCl | F+: 518<br>N1: 4.53(2H, S), 4.56(2H, s), 6.77–6.85(3H, m), 7.04–7.15(3H, m), 7.37(2H, br), 7.72(4H, m), 10.25(1H, S), 10.68(1H, S) |

TABLE 11-continued
| Ex | A | Sal | Dat |
|---|---|---|---|
| 56 | 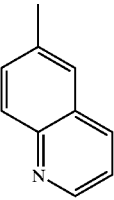 | 2HCl | F+: 498<br>N1: 4.87(2H, s), 7.10(2H, t), 7.16(1H, s), 7.40–7.48 (2H, m), 7.70–7.81(4H, m), 7.82–7.91(2H, m), 8.11–8.21 (2H, m), 8.84(1H, d), 9.13(1H, d), 10.77(1H, s) |
| 57 | 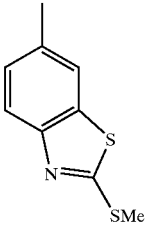 | HCl | F+: 550<br>N1: 2.76(3H, s), 4.72(2H, s), 7.03–7.13(3H, m), 7.28–7.40(3H, m), 7.69–7.76(5H, m), 7.94(1H, d), 10.51(1H, s) |
| 58 | 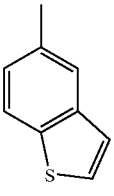 | HCl | F+: 503<br>N1: 4.72(2H, s), 7.06(2H, t), 7.11(1H, s), 7.24(1H, dd), 7.36–7.40(3H, m), 7.73(4H, br), 7.76–7.79(2H, m), 7.90(2H, d), 10.49(1H, s) |
| 59 | Py2 | HCl | F+: 448<br>N1: 4.85(2H, s), 7.01(1H, d), 7.12–7.21(4H, m), 7.38–7.46(2H, m), 7.62–7.68(1H, m), 7.70–7.77(4H, m), 8.38 (1H, d), 10.68(1H, s) |
| 60 | 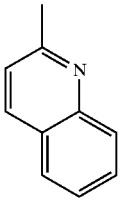 | — | F+: 498<br>N1: 4.98(2H, s), 6.90(1H, s), 7.02(2H, br), 7.13–7.26 (3H, m), 7.50–7.63(5H, m), 7.68–7.77(4H, m), 7.88 (1H, d), 8.16(1H, d), 10.34(1H, s) |
| 61 | 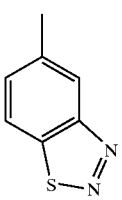 | HCl | F+: 505<br>N1: 4.88(2H, s), 7.09(2H, t), 7.16(1H, s), 7.41–7.50 (2H, m), 7.64–7.71(1H, m), 7.73–7.82(4H, m), 8.30(1H, d), 8.63(1H, d), 10.72(1H, s) |
| 62 | 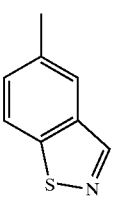 | HCl | F+: 504<br>N1: 4.75(2H, s), 7.05–7.15(3H, m), 7.34–7.48(3H, m), 7.66–7.81(6H, m), 9.71(1H, s), 10.61(1H, s) |

TABLE 11-continued
| Ex | A | Sal | Dat |
|---|---|---|---|
| 63 | | 2HCl | F+: 502<br>N1: 2.88–2.97(2H, m), 3.24–3.36(2H, m), 4.10–4.19 (2H, m), 4.65(2H, s), 7.03–7.21(6H, m), 7.35–7.44(2H, m), 7.70–7.78(4H, m), 10.64(1H, s) |
TABLE 12
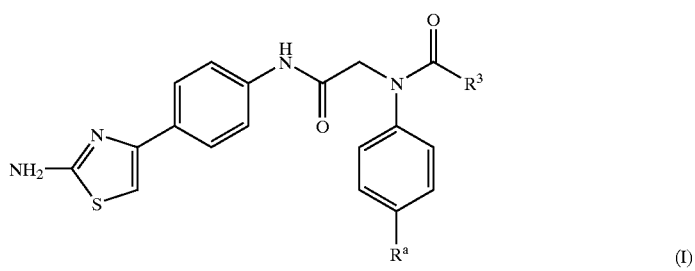
(I)
| Ex | $R^a$ | $R^3$ | Sal | Dat |
|---|---|---|---|---|
| 10 | OMe | 4-CONH$_2$-Ph | HCl | F+: 503 |
| 11 | OMe | 4-COONa-Ph | — | F+: 525 |
| 12 | OMe | 4-OH-Ph | HCl | N1: 3.70(3H, s) 4.57(2H, s), 6.59(2H, d), 6.82(2H d), 7.12–7.15(5H, m), 7.72(4H br), 10.44(1H, s) |
| 13 | OMe | Pipe | 2HCl | F+: 466 |
| 64 | F | cHex | HCl | F+: 453 |
| 65 | OMe | Py2 | 2HCl | F+: 460 |
| 66 | OMe | Py3 | — | F−: 458 |
| 67 | OMe | Py4 | 2HCl | F+: 460<br>N1: 3.68(3H, s), 4.71(2H, s), 6.83(2H, d), 7.18(1H, s), 7.28(2H, d), 7.66–7.82(6H, m), 8.74(2H, d), 10.80(1H, s) |
| 68 | OMe | 4-COOMe-Ph | HCl | F+: 517 |
| 69 | OMe | | 2HCl | F+: 586 |
| 70 | OMe | | HCl | F+: 519 |
| 71 | OMe | tBu | HCl | N1: 0.98(9H, s), 3.77(3H, s), 4.25(2H, s), 6.94–7.00(2H, m), 7.11(1H, s), 7.39–7.45(2H, m), 7.66–7.74(4H, m), 10.27(1H, s) |
| 72 | OMe | | HCl | N1: 1.38–1.47(3H, m), 1.49–1.58(3H, m), 1.66–1.73(6H, m), 1.77–1.83(3H, m), 6.98(2H, d), 7.10(1H, s), 7.40(2H d), 7.66–7.74(4H, m), 10.24(1H, s) |

TABLE 12-continued (Structure I: 2-aminothiazole-phenyl-NH-C(O)-CH2-N(C(O)R³)(phenyl-Rᵃ))

| Ex | Rᵃ | R³ | Sal | Dat |
|---|---|---|---|---|
| 73 | OMe | 4-hydroxycyclohexyl (trans) | HCl | F+: 481 |
| 74 | OMe | 4-hydroxycyclohexyl (cis) | HCl | F+: 481 |

TABLE 13

| Ex | Rᵃ | R³ | Sal | Dat |
|---|---|---|---|---|
| 75 | OMe | 1-Me-Pipe | 2HCl | F+: 480 |
| 76 | OMe | 4-methylquinolinyl | — | N1: 3.32(3H, s), 4.70(2H, s), 6.64(2H, d), 6.92(1H, s), 7.03(2H, br), 7.25'2H, d), 7.41(1H, d), 7.65–7.79(6H, m), 7.95(1H, d), 8.33(1H, d), 8.77 (1H, d), 10.30(1H, s) |
| 77 | OMe | 2,6-Cl₂-Py4 | HCl | N1: 3.70(3H, s), 4.65(2H, s), 6.88(2H, d), 7.13 (1H, d), 7.30(2H, d), 7.42(2H, s), 7.74(4H, m), 10.57(1H, s) |
| 78 | OMe | 2-Cl-Py4 | HCl | F+: 494 |
| 79 | OMe | 4-tetrahydropyranyl | HCl | N1: 1.46–1.49(2H, m), 1.56–1.66(2H, m), 2.5(1H, m), 3.02–3.07(2H, m), 3.74–3.78(5H, m), 4.35 (2H, s), 6.99–7.02(2H, m), 7.09(1H, s), 7.39–7.41 (2H, m), 7.66–7.72(4H, m), 10.30(1H, s) |
| 80 | OMe | 3-tetrahydropyranyl | HCl | F+: 467 |
| 81 | OMe | 2-tetrahydropyranyl | HCl | F+: 467 |
| 82 | OMe | 4-methylchroman-4-yl | HCl | N1: 1.93–2.10(2H, m), 3.78–3.86(4H, m), 3.93–3.98 (1H, m), 4.25–4.30(1H, m), 4.38(1H, d), 4.52 (1H, d), 6.71(1H, d), 6.82–6.85(1H, m), 7.04–7.16 (5H, m), 7.57(2H, d), 7.68–7.74(4H, m), 10.39 (1H, s) |
| 83 | OMe | 4-tetrahydrothiopyranyl | HCl | F+: 483  N1: 1.62–1.70(2H, m), 1.90–1.93(2H, m), 2.30–2.37 (3H, m), 2.53–2.54(2H, m), 3.78(3H, s), 4.33 (2H, s), 7.00(2H, d), 7.09(1H, s), 7.38(2H, d), 7.66–7.72(4H, m), 10.30(1H, s) |

TABLE 13-continued

| Ex | R$^a$ | R$^3$ | Sal | Dat |
|---|---|---|---|---|
| 84 | OMe | (4-tetrahydrothiopyran-1-oxide) | HCl | F+: 499 |
| 85 | OMe | (4-tetrahydrothiopyran-1,1-dioxide) | HCl | F+: 515<br>N1: 2.00–2.08(4H, m), 2.63–2.70(iH, m), 2.93–3.05 (4H, m), 3.78(3H, s), 4.36(2H, s), 7.01(2H, d), 7.11(1H, s), 7.40(2H, d), 7.67–7.73(4H, m), 10.37(1H, s) |
| 86 | Cl | (4-tetrahydrothiopyran-1,1-dioxide) | HCl | F+: 519<br>N1: 2.0(4H, m), 2.68–2.73(1H, m), 3.00–3.02(4H, m), 4:40(2H, s), 7.12(1H, s), 7.50–7.56(4H, m), 7.68–7.74(4H, m), 10.44(1H, s) |
| 87 | OMe | 4-OH-cHex | HCl | N1: 0.76–0.84(1H, m), 1.08–1.14(1H, m), 1.31–1.43 (2H, m), 1.57–1.66(2H, m), 1.75–1.81(2H, m), 2.1(1H, m), 2.2(1H, m), 3.3(1H, m), 3.7(1H, m), 4.34 (1H, s), 6.98–7.01(2H, m), 7.11(1H, s), 7.38(2H, d), 7.67–7.73(4H, m), 10.33(1H, s) |

TABLE 14

| Ex | R$^a$ | R$^3$ | Sal | Dat |
|---|---|---|---|---|
| 88 | Br | (4-tetrahydrothiopyran-1,1-dioxide) | HCl | F+: 563<br>N1: 1.96–2.10(4H, m), 2.65–2.76(1H, m), 2.93–3.13 4H, m), 4.39(2H, s), 7.11(1H, s), 7.45(2H, d), 7.62–7.80(6H, m), 10.41(1H, s) |
| 89 | SMe | (4-tetrahydrothiopyran-1,1-dioxide) | HCl | F+: 531<br>N1: 1.95–2.12(4H, m), 2.50(3H, s), 2.66–2.76(1H, m), 2.90–3.10(4H, m), 4.38(2H, s), 7.11(1H, s), 7.34(2H, d), 7.42(2H, d), 7.65–7.77(4H, m), 10.39 (1H, s) |
| 90 | OMe | (thiocane-1,1-dioxide) | HCl | F+: 543<br>N1: 1.54–1.56(2H, m), 1.63–1.80(4H, m), 2.56–2.60 (1H, m), 2.79–2.85(2H, m), 3.10–3.15(2H, m), 3.78(3H, s), 4.35(2H, 7.00–7.03(2H, m), 7.10(1H, s), 7.40–7.43(2H, m), 7.67–7.73(4H, m), 10.34 (1H, m) |
| 91 | OMe | (benzothiopyran-1,1-dioxide) | HCl | F+: 563<br>N1: 2.41–2.51(2H, m), 3.49–3.61(2H, m), 3.78(3H, s), 4.13(1H, t), 4.40(1H, d), 4.52(1H, d), 7.05–7.10 (3H, m), 7.47–7.53(2H, m), 7.58–7.64(3H, m) 7.68–7.78(5H, m), 10.42(1H, s) |

TABLE 15
| Ex | Str | Sal | Dat |
|---|---|---|---|
| 92 | 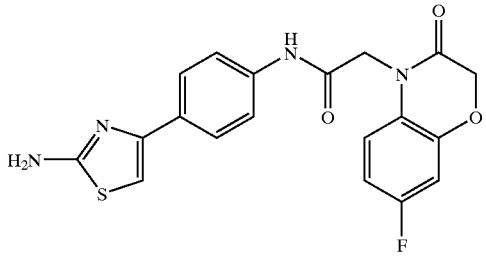 | HCl | N1: 4.76(2H, s), 4.79(2H, s), 6.90(1H, dt), 7.00(1H, dd), 7.10–7.13(2H, m), 7.69(2H, d), 7.74(2H, d), 10.70 (1H, s) |
| 93 | 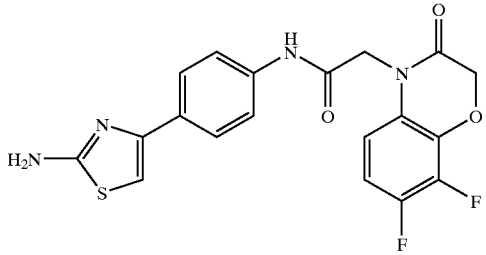 | HCl | N1: 4.81(2H, s), 4.88(2H, s), 6.94–6.97 (1H, m), 7.08–7.14(2H, m), 7.69 (2H, d), 7.74(2H, d), 10.73(1H,s) |
| 94 | 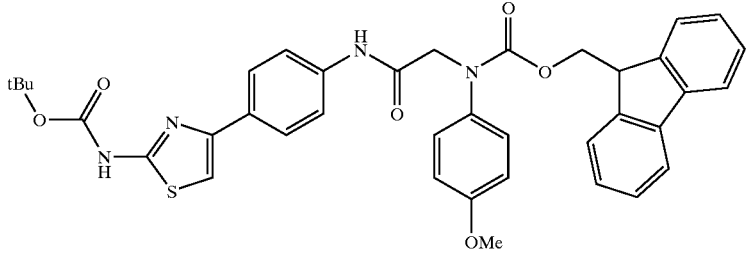 | — | F−: 675 |
| 95 | 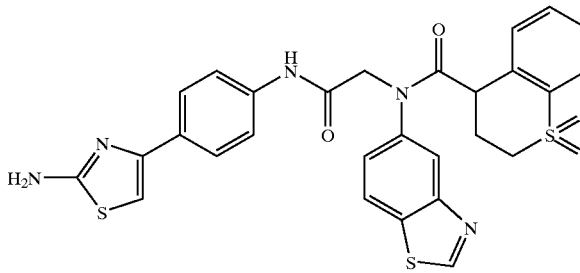 | — | F+: 590<br>N1: 2.47–2.59(2H, m), 3.48–3.60(2H, m), 4.18–4.21(1H, m), 4.50(1H, d), 4.56(1H, d), 6.90(1H, s), 7.02 (1H, s), 7.49–7.53(1H, m), 7.57–7.66 (4H, m), 7.73–7.77(3H, m), 7.82(1H, d), 8.33(1H, d), 8.43(1H, br), 9.50 (1H, s), 10.19(1H, s) |
TABLE 16
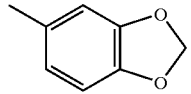
(I)
| Ex | R¹ | R² | A | Sal | Dat |
|---|---|---|---|---|---|
| 14 | Me | H | 4-F-Ph | — | F−: 462 |
| 15 | NHAc | H | (3,4-methylenedioxyphenyl) | — | F+: 533 |

TABLE 16-continued

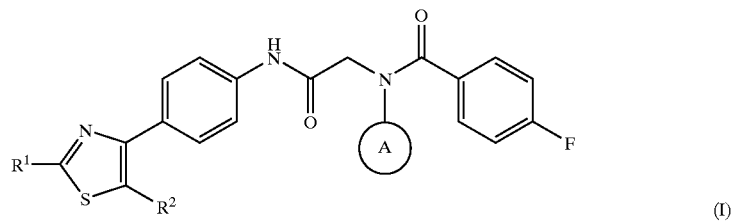

(I)

| Ex | R¹ | R² | A | Sal | Dat |
|---|---|---|---|---|---|
| 16 | -NH(Me)C(O)CH₂NH₂ | H | 5-methyl-benzo[1,3]dioxole | HCl | F+: 548 |
| 17 | NH₂ | Br | 4-F-Ph | HCl | E: 543 |
| 96 | CO₂Et | H | 4-F-Ph | — | F+:522 |
| 97 | NH₂ | CO₂Et | 4-F-Ph | HCl | F: 356 |
| 98 | NH—Me | H | 4-F-Ph | HCl | F+: 479 |
| 99 | NH-Ph | H | 4-F-Ph | HBr | F+: 451 |
| 100 | NH-Py2 | H | 4-F-Ph | 2HCl | F+: 542 |
| 101 | piperidin-1-yl | H | 4-F-Ph | HCl | F+: 533 |
| 102 | N(Me)NH₂ | H | 4-F-Ph | HCl | F+: 494 |
| 103 | -NH-C(=NH)-NH₂ (methylguanidine) | H | 4-F-Ph | HCl | F+: 507 |
| 104 | -NH(Me)C(O)CH₂NH₂ | H | benzothiazol-6-yl | HCl | N1: 3.91(2H, s), 4.75(2H, s), 7.08 (2H, t), 7.37–7.42(3H, m), 7.61(1H, s), 7.71(2H, d), 7.85(2H, d), 7.97(1H, d), 8.11(1H, d), 8.37(2H, br), 9.39(1H, s), 10.44(1H, s), 12.74(1H, s) |
| 105 | NHMe | H | benzothiazol-6-yl | HCl | N1: 3.00(3H, s), 4.75(2H, s), 7.05–7.09(3H, m), 7.36–7.42(3H, m), 7.71(1H, d), 7.76(1H, d), 7.97(1H, d), 8.11(1H, d), 9.37(1H, s), 10.50 (1H, s) |
| 106 | NMe₂ | H | benzothiazol-6-yl | HCl | F+: 532 |

TABLE 17

| Ex | Str | Sal | Dat |
|---|---|---|---|
| 18 | | HCl | F+: 508 |
| 107 | | 2HCl | N1: 4.86(2H, s), 7.19(1H, s), 7.54 (1H, d), 7.76–7.87(6H, m), 7.99(1H, d), 8.75(2H, m), 9.41(1H, s), 10.90 (1H, s) |
| 108 | | 2HCl | F+: 487<br>N1: 4.86(2H, s), 7.18(1H, s), 7.49 (1H, d), 7.78(6H, m), 8.09–8.13(2H, m), 8.71(2H, d), 9.43(1H, s), 10.83 (1H, s) |
| 109 | | — | F+: 506 |
| 110 | | HCl | F+: 494<br>N1: 1.51–1.54(2H, m), 1.60–1.70(2H, m), 2.53–2.56(1H, m), 2.98–3.04 (2H, m), 3.73–3.75(2H, m), 4.48(2H, s), 7.10(1H, d), 7.63(1H, d), 7.68–7.73(4H, m), 8.23(1H, s), 8.27(1H, d), 9.49(1H, s), 10.37(1H, s) |

TABLE 17-continued

| Ex | Str | Sal | Dat |
|---|---|---|---|
| 111 | | HCl | F+: 510<br>N1: 1.65–1.74(2H, m), 1.97–2.00(2H, m), 2.28–2.48(5H, m), 4.47(s, 2H), 7.11(1H, s), 7.61(1H, d), 7.69–7.74(4H, m), 8.21(1H, s), 8.27(1H, d), 9.50(1H, s), 10.40(1H, s) |
| 112 | | HCl | N1: 2.05–2.06(4H, m), 2.72–2.78(1H, m), 2.93–2.99(4H, m), 4.49(2H, s), 7.11(1H, s), 7.63(1H, dd), 7.69–7.74(4H, m), 8.23(1H, d), 8.28(1H, d), 9.50(1H, s), 10.42(1H, s) |
| 113 | | HCl | F+: 558<br>N1: 2.07–2.18(2H, m), 2.84–2.90(1H, m), 3.09–3.15(1H, m), 3.83–3.86(1H, m), 4.52(1H, d), 4.62(1H, d), 7.01–7.10(4H, m), 7.30(1H, d), 7.72–7.83(5H, m), 8.31(1H, d), 8.38(1H, d), 9.50(1H, s), 10.44(1H, s) |

TABLE 18

| Ex | Str | Sal | Dat |
|---|---|---|---|
| 114 | | HCl | F+: 492<br>N1: 0.83–1.70(10H, m), 2.24(1H, m), 4.46(2H, s), 7.11(1H, s), 7.65(1H, d), 7.71(4H, m), 8.17(1H, d), 8.30(1H, s), 9.47(1H, s), 10.39(1H, s) |
| 115 | | HCl | F+: 508<br>N1: 1.65–1.80(1H, m), 1.83–2.27(6H, m), 4.51(2H, m), 507–5.18(1H, m), 7.13(1H, m), 7.61–7.76(5H, m), 8.20–8.32(2H, m), 9.50(1H, s), 10.45(1H, s) |

TABLE 18-continued
| Ex | Str | Sal | Dat |
|---|---|---|---|
| 116 | 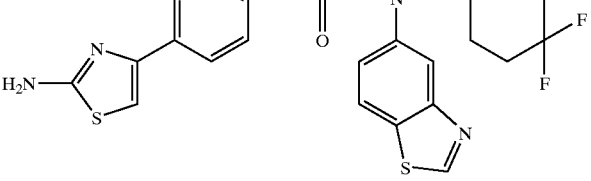 | HCl | F+: 528<br>N1: 1.44–2.02(8H, m), 2.40–2.60(1H, m), 4.49(2H, s), 7.11(1H, s), 7.59–7.78 (5H, m), 8.19–8.34(2H, m), 9.49(1H, s), 10.40(1H, s) |
| 117 | 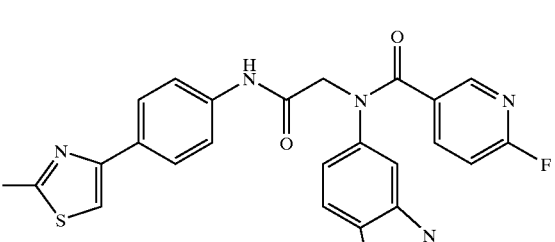 | HCl | F+: 505<br>N1: 4.80(2H, s), 7.08–7.12(2H, m), 7.44 (1H, d), 7.73(4H, br), 7.9(1H, m), 8.05–8.19(3H, m), 9.43(1H, s), 10.56 (1H, s) |
| 118 | 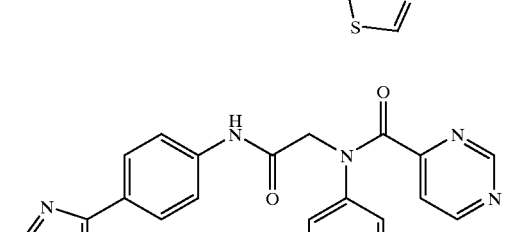 | HCl | F+: 488<br>N1: 4.82(2H, s), 7.16(1H, s), 7.42(1H, d), 7.63(1H, d), 7.75(4H, br), 8.03–8.06 (2H, m), 8.79(1H, d), 8.98(1H, s), 9.40(1H, s), 10.66(1H, s) |
| 119 | 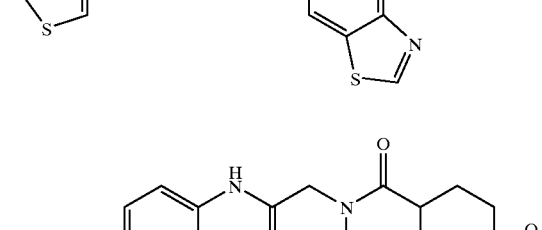 | HCl | F+: 525<br>N1: 1.95–2.15(6H, m), 2.67–2.78(1H, m), 2.79–3.13(6H, m), 4.37(2H, s), 7.13 (1H, s), 7.18–7.23(1H, m), 7.27–7.34(2H, m), 7.68–7.78(4H, m), 10.42(1H, s) |
| 120 | 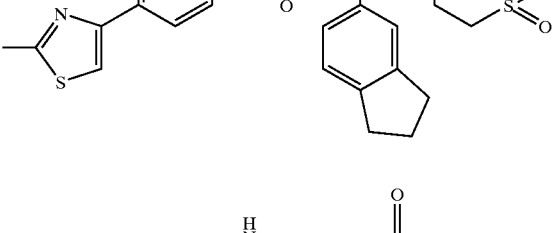 | HCl | F+: 542<br>N1: 2.05–2.06(4H, m), 2.70–2.77(1H, m), 3.0(4H, m), 4.48(2H, s), 7.14(1H, s), 7.67(1H, dd), 7.70–7.75(4H, m), 8.17(1H, d), 8.31(1H, d), 9.48(1H, s), 10.48(1H, s) |

TABLE 18-continued

| Ex | Str | Sal | Dat |
|---|---|---|---|
| 121 | 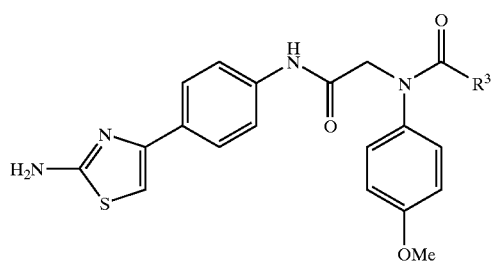 | HCl | F+: 543<br>N1: 2.00–2.05(4H, m), 2.68–2.75(1H, m), 2.97–3.03(4H, m), 4.26(4H, br), 4.34(2H, s), 6.91–6.95(2H, m), 7.02(1H, d), 7.11(1H, s), 7.67–7.73(4H, m), 10.37(1H, s) |

TABLE 19

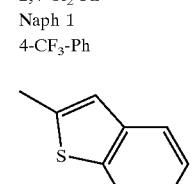

(I)

| Ex | R³ | Dat |
|---|---|---|
| a-1 | 2-Me-Ph | A+: 473 |
| a-2 | 2,6-F₂-Ph | A+: 495 |
| a-3 | 2,3-F₂-Ph | A+: 495 |
| a-4 | 2-Cl-Ph | A+: 493 |
| a-5 | 2-CF₃-Ph | A+: 527 |
| a-6 | Ph | E+: 459 |
| a-7 | 3-Me-Ph | E+: 473 |
| a-8 | 3-Br-Ph | E+: 538 |
| a-9 | 3,5-Cl₂-Ph | E+: 528 |
| a-10 | 2-F-Ph | E+: 477 |
| a-11 | 3-Cl-Ph | E+: 493 |
| a-12 | 3-OCF₃-Ph | E+: 543 |
| a-13 | 3,5-F₂-Ph | E+: 495 |
| a-14 | 2,4-F₂-Ph | E+: 495 |
| a-15 | 3,4-F₂-Ph | E+: 495 |
| a-16 | 3-F-Ph | E+: 477 |
| a-17 | 4-CO₂Me-Ph | E+: 515 |
| a-18 | 2-OMe-Ph | E+: 489 |
| a-19 | 2-CO₂Me-Ph | E+: 517 |
| a-20 | 4-Me-Ph | E+: 473 |
| a-21 | 3-CF₃-Ph | E+: 527 |
| a-22 | 3,4-Cl₂-Ph | E+: 528 |
| a-23 | 2,4-Cl₂-Ph | E+: 528 |
| a-24 | Naph 1 | E+: 509 |
| a-25 | 4-CF₃-Ph | E+: 527 |
| a-26 | (2-methylbenzothiophene) | E+: 515 |
| a-27 | Th2 | E+: 465 |
| a-28 | Fu | E+: 449 |

TABLE 20

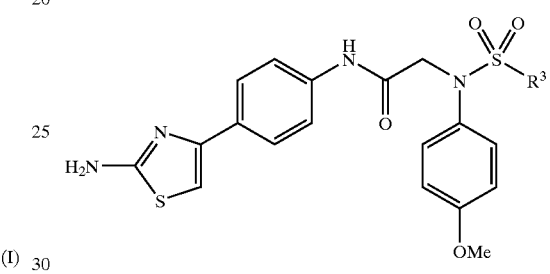

(I)

| Ex | R³ | Dat |
|---|---|---|
| b-1 | Ph | A+: 495 |
| b-2 | 2,4-F₂-Ph | A+: 531 |
| b-3 | Me | A+: 433 |
| b-4 | Et | A+: 447 |
| b-5 | Pr | A+: 461 |
| b-6 | iPr | A+: 461 |
| b-7 | 3-F-Ph | A+: 513 |
| b-8 | 4-Cl-Ph | A+: 529 |
| b-9 | 3-Cl-Ph | A+: 529 |
| b-10 | 2-Cl-Ph | A+: 529 |
| b-11 | 3-Me-Ph | A+: 509 |
| b-12 | 4-Pr-Ph | A+: 537 |

TABLE 21

| Ex | R³ | Dat |
|---|---|---|
| b-13 | Bu | A+: 475 |
| b-14 | NMe₂ | A+: 538 |
| b-15 | 4-tBu-Ph | A+: 551 |
| b-16 | 4-NHAc-Ph | A+: 552 |
| b-17 | 4-OCF₃-Ph | A+: 579 |
| b-18 | 4-Bu-Ph | A+: 567 |
| b-19 | 3-CN-Ph | A+: 520 |
| b-20 | 2-CN-Ph | A+: 520 |
| b-21 | 4-CO₂H-Ph | A+: 539 |
| b-22 | 3-CO₂H-Ph | A+: 539 |
| b-23 | 4-CF₃-Ph | A+: 563 |
| b-24 | 3-CF₃-Ph | A+: 563 |
| b-25 | 2-CF₃-Ph | A+: 563 |
| b-26 | 4-NO₂-Ph | A+: 540 |
| b-27 | 3-NO₂-Ph | A+: 540 |
| b-28 | 2-NO₂-Ph | A+: 540 |
| b-29 | 4-Br-Ph | A+: 573 |
| b-30 | 2-Br-Ph | A+: 573 |
| b-31 | 4-F-Ph | A+: 513 |

TABLE 21-continued

| Ex | R³ | Dat |
|---|---|---|
| b-32 | (E)-styryl | A+: 521 |
| b-33 | 2,5-Br₂-Ph | A+: 652 |
| b-34 | 5-F-2-Me-Ph | A+: 527 |
| b-35 | 3,5-(CF₃)₂-Ph | A+: 631 |
| b-36 | 4-OMe-2-NO₂-Ph | A+: 570 |
| b-37 | 2,5-(Me)₂-Ph | A+: 523 |
| b-38 | 2-OMe-4-Me-Ph | A+: 539 |
| b-39 | 2,5-(OMe)₂-Ph | A+: 555 |
| b-40 | Naph1 | A+: 545 |
| b-41 | 3-Br-2,5-Cl₂-4-Me-thienyl | A+: 649 |
| b-42 | 4-iPr-Ph | A+: 537 |
| b-43 | 2,4,5-Cl₃-Ph | A+: 597 |
| b-44 | 3,5-Cl₂-Ph | A+: 564 |
| b-45 | 3,4-Cl₂-Ph | A+: 564 |
| b-46 | 2,5-Cl₂-Ph | A+: 564 |
| b-47 | 2,6-Cl₂-Ph | A+: 564 |
| b-48 | 2,4-Cl₂-Ph | A+: 564 |
| b-49 | 2,3,4-Cl₃-Ph | A+: 597 |
| b-50 | 2,3-Cl₂-Ph | A+: 564 |
| b-51 | 3-Cl-2-Me-Ph | A+: 544 |
| b-52 | 3-Cl-2-F-Ph | A+: 548 |
| b-53 | 2-Cl-5-CF₃Ph | A+: 598 |
| b-54 | 3,5-Cl₂-OH-Ph | A+: 580 |
| b-55 | 5-Cl-2-OMe-Ph | A+: 560 |
| b-56 | 2-Cl-4-CN-Ph | A+: 555 |
| b-57 | 4-Cl-3-NO₂-Ph | A+: 575 |
| b-58 | 4-Br-2-Et-Ph | A+: 602 |
| b-59 | 2,5-Br₂-3,6-F₂-Ph | A+: 689 |
| b-60 | 4-Br-2,5-F₂-Ph | A+: 610 |
| b-61 | 3-Br-2-Cl-5-Me-pyridyl | A+: 609 |
| b-62 | 5-Br-2-OMe-Ph | A+: 604 |
| b-63 | 4-CO₂Me-3-OMe-Th2 | A+: 589 |
| b-64 | 5-Pyr-Th2 | A+: 578 |
| b-65 | 3-Br-5-Cl-Th2 | A+: 613 |
| b-66 | 5-Cl-Th2 | A+: 536 |
| b-67 | Th2 | A+: 501 |
| b-68 | 2,3,5,6-(Me)₄-Ph | A+: 551 |
| b-69 | 4-Ph-Ph | A+: 571 |
| b-70 | 5-Me-2-NHAc-thiazolyl | A+: 573 |

TABLE 22

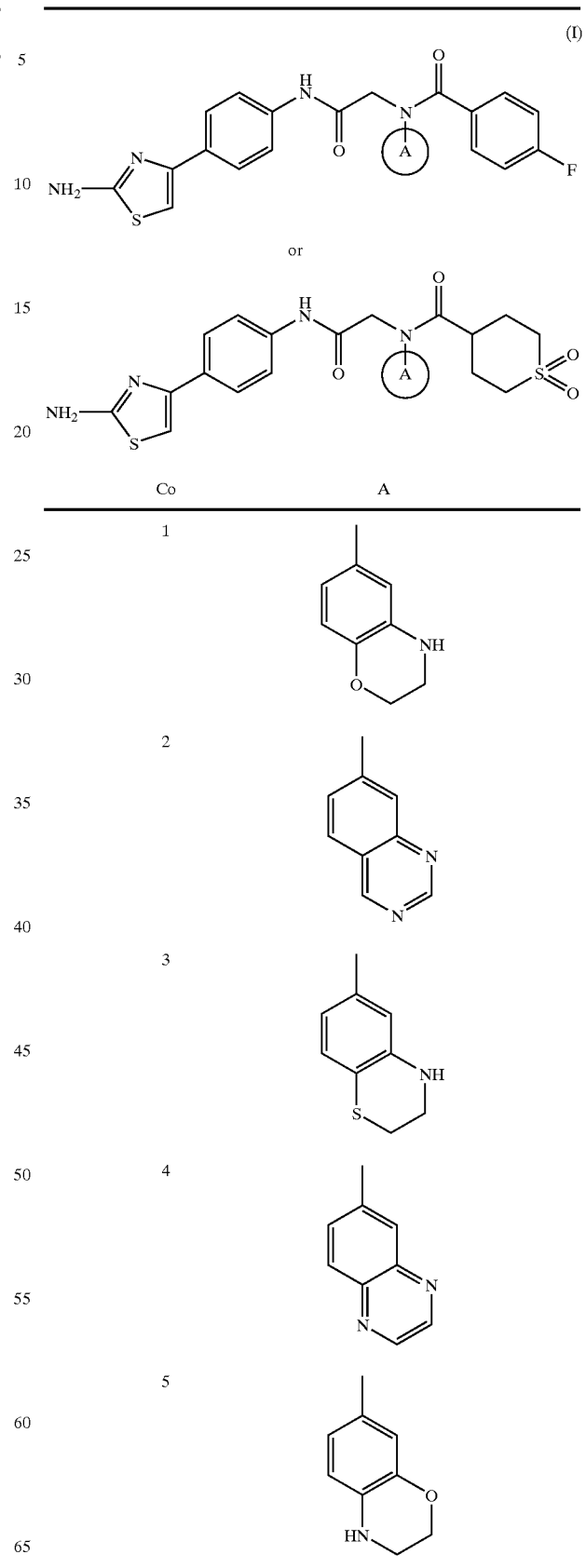

| Co | A |
|---|---|
| 1 | 3,4-dihydro-2H-benzo[b][1,4]oxazin-6-yl |
| 2 | quinazolin-6-yl |
| 3 | 3,4-dihydro-2H-benzo[b][1,4]thiazin-6-yl |
| 4 | quinoxalin-6-yl |
| 5 | 3,4-dihydro-2H-benzo[b][1,4]oxazin-7-yl |

TABLE 22-continued
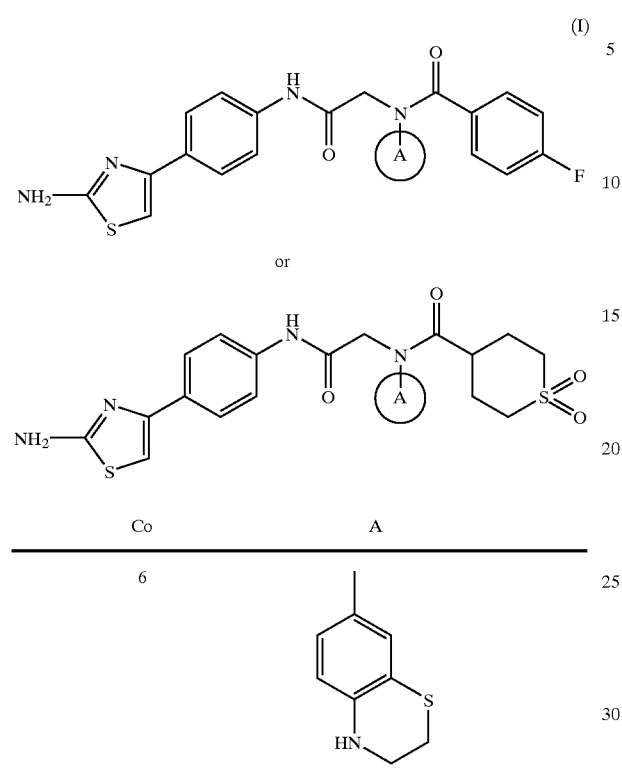
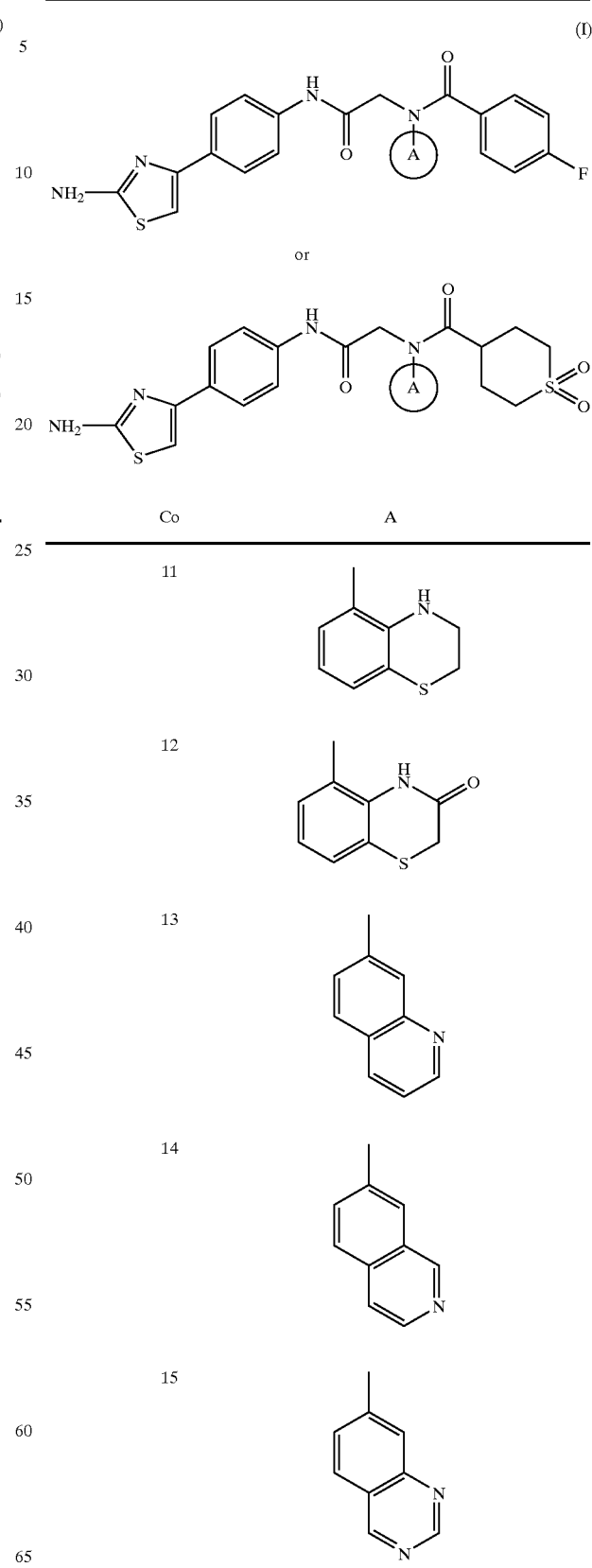

TABLE 22-continued
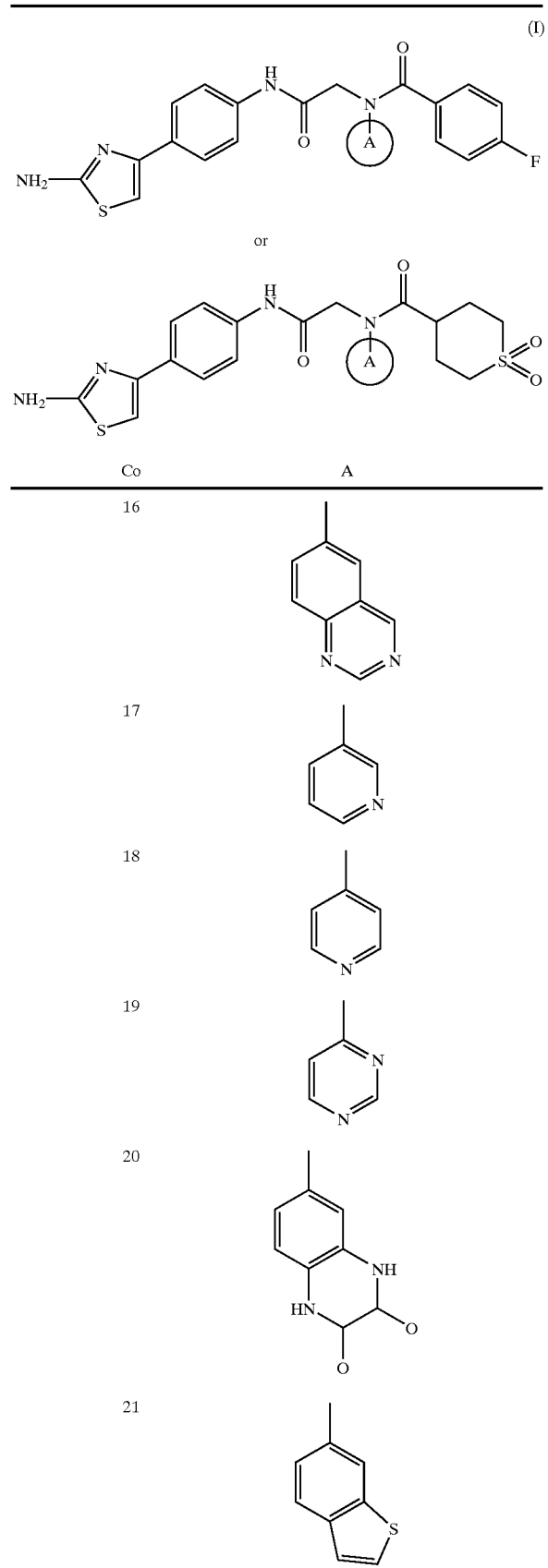
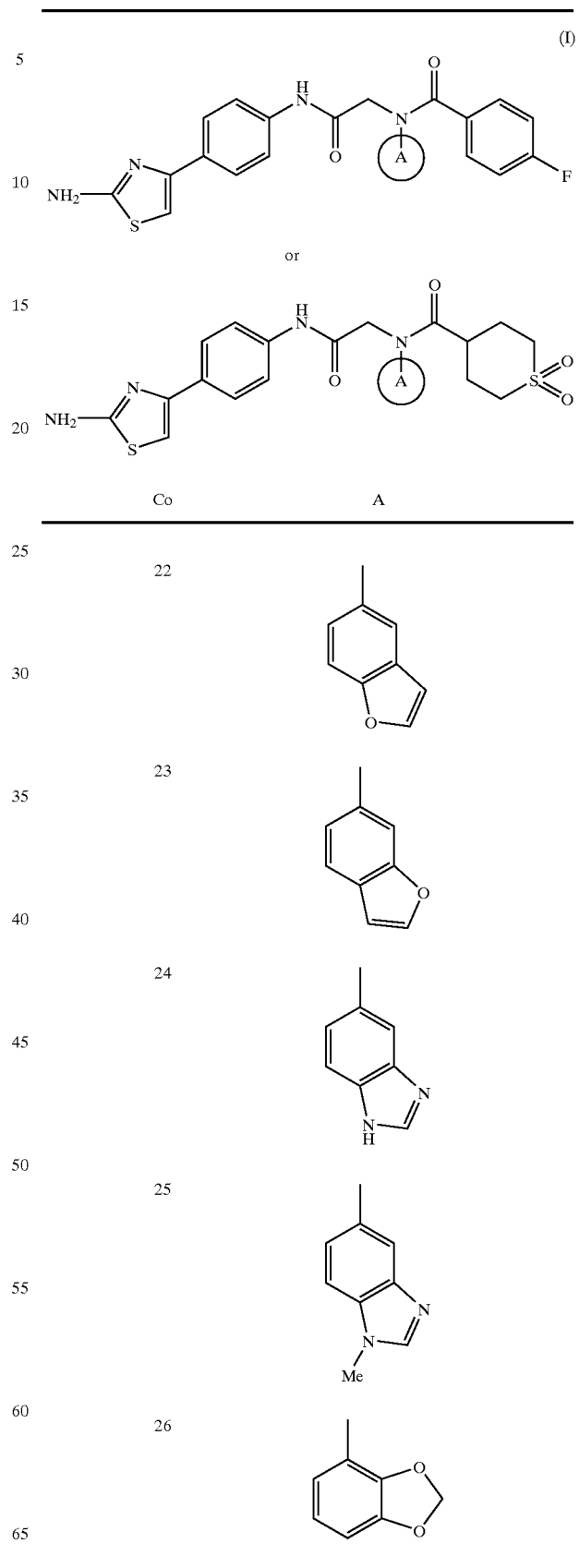

TABLE 22-continued
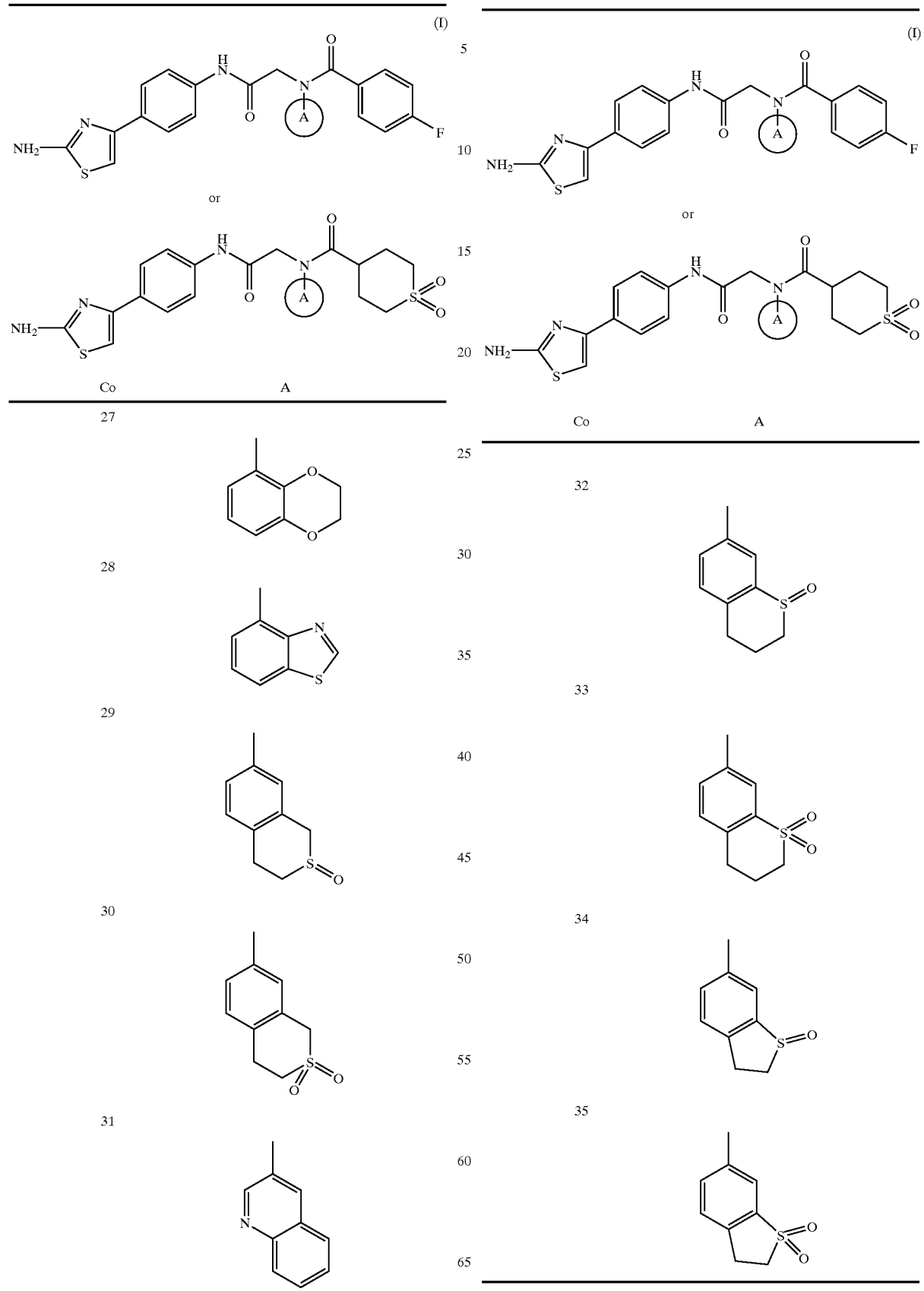

TABLE 23
| Co | A |
|---|---|
| 36 | 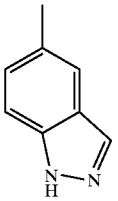 |
| 37 | 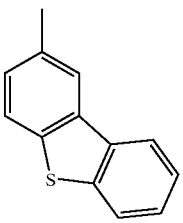 |
| 38 | 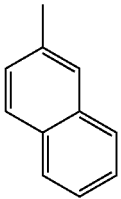 |
| 39 | 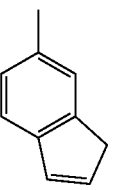 |
| 40 | 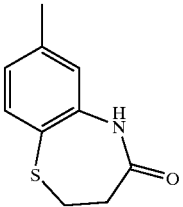 |
| 41 | 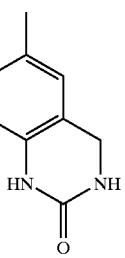 |
| 42 | 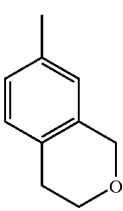 |
TABLE 23-continued
| Co | A |
|---|---|
| 43 | 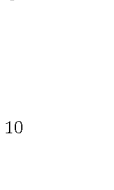 |
| 44 |  |
| 45 |  |
| 46 |  |
| 47 |  |
| 48 |  |
| 49 | 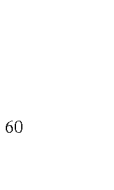 |

TABLE 23-continued
| Co | A |
|---|---|
| 50 | 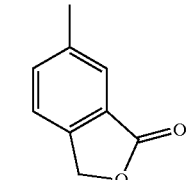 |
| 51 | 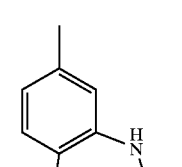 |
| 52 | 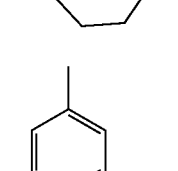 |
| 53 | 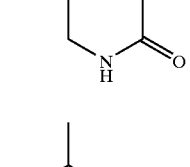 |
| 54 | 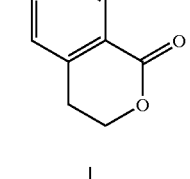 |
| 55 | 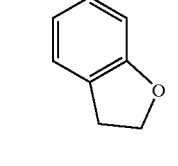 |
TABLE 23-continued
| Co | A |
|---|---|
| 56 | 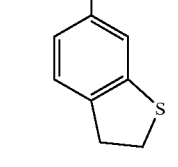 |
| 57 | 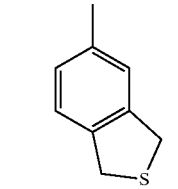 |
| 58 | |
| 59 | |
| 60 | |
| 61 | |
| 62 | |

TABLE 23-continued

| Co | A |
|---|---|
| 63 | 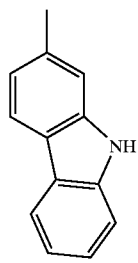 |
| 64 | 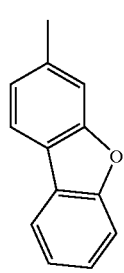 |
| 65 | 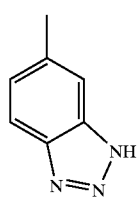 |
| 66 | 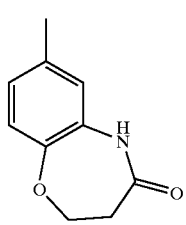 |
| 67 | 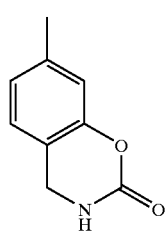 |
| 68 | 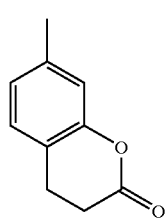 |

TABLE 23-continued

| Co | A |
|---|---|
| 69 | ![structure] |

TABLE 24

(I)

[Two structures shown for formula (I): 2-amino-thiazole-phenyl-NH-CO-CH2-N(Ar)-C(O)-R³ where Ar = 4-methoxyphenyl or benzothiazol-5-yl]

| Co | R³ |
|---|---|
| 70 | 2-Cl-4-NO$_2$-Ph |
| 71 | CH$_2$(4-Cl-Ph) |
| 72 | 2-OAc-Ph |
| 73 | 3-CN-Ph |
| 74 | 2,5-F$_2$-Ph |
| 75 | 4-OMe-Ph |
| 76 | 4-NO$_2$-Ph |
| 77 | 2,6-F$_2$-Ph |
| 78 | 2,3,4,5,6-F$_5$-Ph |
| 79 | 3,4-(OMe)$_2$-Ph |
| 80 | 4-CN-Ph |
| 81 | 2-NO$_2$-Ph |
| 82 | 4-Br-Ph |
| 83 | OCH$_2$(4-NO$_2$-Ph) |
| 84 | 4-OMe-cHex |
| 85 | 2-NHAc-Ph |
| 86 | 4-Br-2-Me-Ph |
| 87 | 3-Br-4-Me-Ph |
| 88 | 4-Cl-3-NO$_2$-Ph |
| 89 | 5-CO$_2$H-2-F-Ph |
| 90 | 3-Cl-4-Me-Ph |
| 91 | 2,4,6-(OMe)$_3$-Ph |
| 92 | 2-Ac-Ph |
| 93 | 3-NMe$_2$-Ph |
| 94 | 3-OPh-Ph |
| 95 | 2-Br-5-OMe-Ph |
| 96 | 4-CO$_2$H-2-Me-Ph |
| 97 | 3-OMe-2-NO$_2$-Ph |
| 98 | 2-CO$_2$H-4-Cl-Ph |
| 99 | 3-OMe-4-Me-Ph |
| 100 | Th3 |
| 101 | 5-Br-Th2 |
| 102 | Pyrr |
| 103 | 3,5-(OMe)$_2$-Ph |

TABLE 24-continued (I)

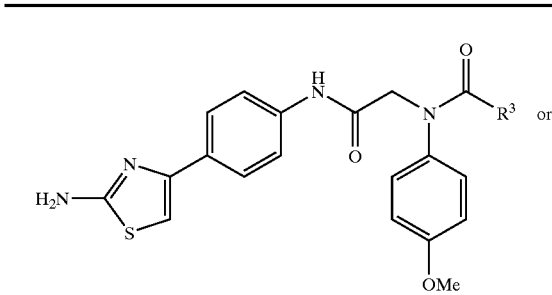

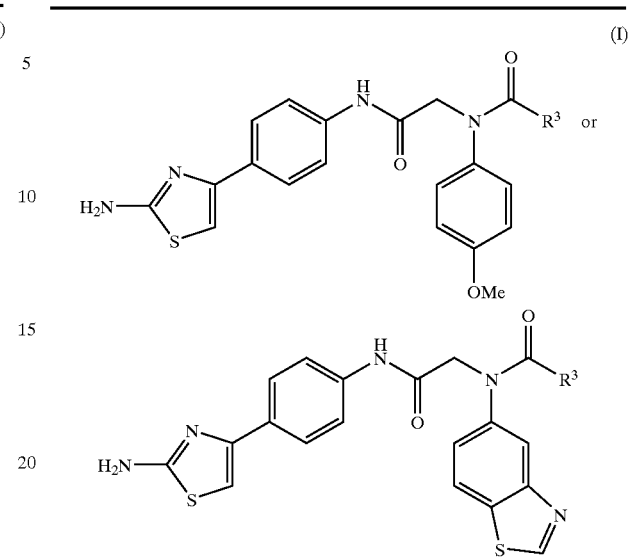

| Co | R³ |
|---|---|
| 104 | 2-COPh-Ph |
| 105 | CH₂CH₂CO₂Me |
| 106 | CH=CHCO₂Et |
| 107 | CH(cHex)₂ |
| 108 | 2-OMe-Ac |
| 109 | CH₂CH₂CH₂CO₂Me |
| 110 | CH₂CH₂CH₂Ph |
| 111 | COCH₂Ph |
| 112 | CH₂(3-NO₂-Ph) |
| 113 | CH₂(2-Cl-Ph) |
| 114 | CH₂(2-F-Ph) |
| 115 | CH₂(2-Me-Ph) |
| 116 | CH₂(2-OMe-Ph) |
| 117 | CH₂(Naph1) |
| 118 | CH₂(3,4-(OMe)₂-Ph) |
| 119 | CH₂(3,4,5-(OMe)₃-Ph) |
| 120 | CH₂-cHex |
| 121 | CH₂(2-NO₂-Ph) |
| 122 | CH₂(4-NO₂-Ph) |
| 123 | CH₂(3-Cl-Ph) |
| 124 | CH₂(2-Br-Ph) |
| 125 | CH₂(3-Me-Ph) |
| 126 | CH₂(3-OMe-Ph) |
| 127 | CH₂(Th3) |
| 128 | CH₂(Naph2) |
| 129 | CH₂(2,4-Cl-Ph) |
| 130 | 4-Cl-Ph |
| 131 | 3-OMe-Ph |
| 132 | 3-CO₂Me-Ph |
| 133 | 4-iPr-Ph |
| 134 | 5-NO₂-Fu |
| 135 | 6-Me-Py2 |
| 136 | Py2 |
| 137 | Py4 |
| 138 | Py3 |
| 139 | NO₂-Ph |
| 140 | Me |
| 141 | Et |
| 142 | iPr |
| 143 | tBu |
| 144 | iBu |
| 145 | Hep4 |
| 146 | cBu |
| 147 | cHex |
| 148 | cPen |
| 149 | CCl₃ |
| 150 | Naph2 |
| 151 | 4-Ph-Ph |
| 152 | 2-F-Ph |
| 153 | 2-Br-Ph |

TABLE 24-continued (I)

| Co | R³ |
|---|---|
| 154 | CH(Ph)₂ |
| 155 | 4-Me-Ph |
| 156 | 2-CO₂Me-Ph |
| 157 | 4-CO₂Me-Ph |
| 158 | 5-Cl-Th2 |
| 159 | 3-Me-Th2 |
| 160 | 1-Me-Pyrr |
| 161 | Fu |
| 162 | Pyra |
| 163 | Ind5 |
| 164 | 4-Bu-Ph |
| 165 | 2-OPh-Ac |
| 166 | 3-CF₃-Ph |
| 167 | 4-Ac-Ph |
| 168 | Ind3 |

TABLE 25

| Co | R³ |
|---|---|
| 169 | 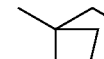 |
| 170 | 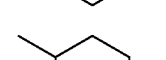 |
| 171 | 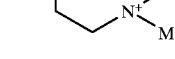 |
| 172 | 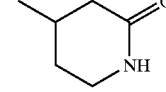 |

TABLE 25-continued

| Co | R³ |
|---|---|
| 173 | 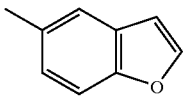 |
| 174 | 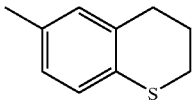 |
| 175 | 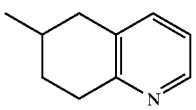 |
| 176 | 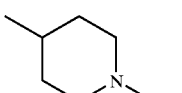 |
| 177 | 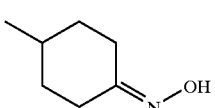 |
| 178 | 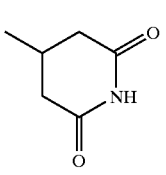 |
| 179 | 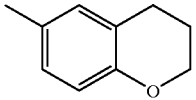 |
| 180 | 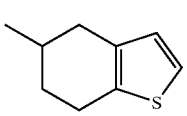 |
| 181 | 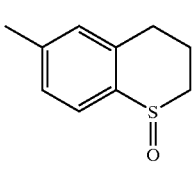 |
| 182 | 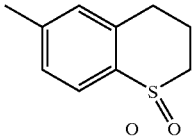 |
| 183 | 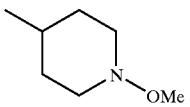 |
| 184 | 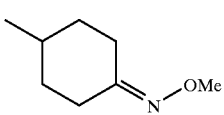 |
| 185 | 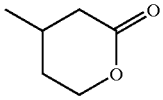 |
| 186 | 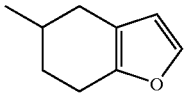 |
| 187 | 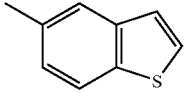 |

What is claimed is:

1. An amide derivative represented by the following general formula (I) or a salt thereof

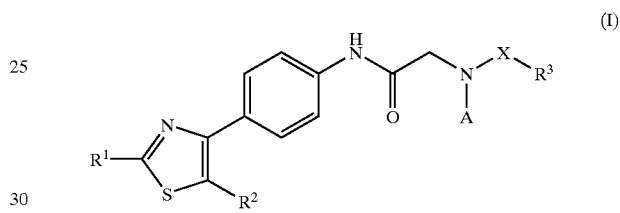

(symbols in the formula have the following meanings; $R^1$ and $R^2$: the same or different from each other, and each represents —H, -lower alkyl, -lower alkenyl, -lower alkynyl, -cycloalkyl, -cycloalkenyl, —NRaRb, —NRc-NRaRb, —NRc-(nitrogen-containing saturated heterocyclic ring which may be substituted with lower alkyl), —NRc-C(=NH)—NRaRb, -(nitrogen-containing saturated heterocyclic ring which may be substituted with lower alkyl , -lower alkylene-NRaRb, -lower alkylene-(nitrogen-containing saturated heterocyclic ring which may be substituted with lower alkyl), —NRaCORb, —NRaCO—ORb, —NRaCO—NRbRc, —NRaCO-lower alkylene-NRbRc, —NRaCO-lower alkylene-(nitrogen-containing saturated heterocyclic ring which may be substituted with lower alkyl), —NRaSO₂Rb, —NRaSO₂—NRbRc, —NRaSO₂-lower alkylene-NRbRc, —NRaSO₂-lower alkylene-(nitrogen-containing saturated heterocyclic ring which may be substituted with lower alkyl), —CONRaRb, —SO₂NRaRb, —COORa, —SO₂Ra, —CONRa—ORb, —OCORa, —ORa, -halogen, —CORa, —NO₂, —CN or -halogeno lower alkyl, Ra, Rb and Rc: the same or different from one another, and each represents —H, -lower alkyl, -lower alkenyl, -lower alkynyl, -cycloalkyl, -cycloalkenyl, -aryl, -5- or 6- membered monocyclic heteroaryl or -lower alkylene-aryl, A: -aryl which may have one or more substituents, -heteroaryl which may have one or more substituents, -saturated carbon ring-condensed aryl which may have one or ore substituents or -saturated heterocyclic ring-condensed aryl which may have one or more substituents, wherein the saturated carbon ring-condensed aryl and saturated heterocyclic ring-condensed aryl bind to the adjacent N atom via C atom of the aromatic ring,

93

X: CO or SO₂,

R³: -alkyl which may have one or more substituents, -alkenyl which may have one or more substituents, -alkynyl which may have one or more substituents, -cycloalkyl which may have one or more substituents, -cycloalkenyl which may have one or more substituents, -aryl which may have one or more substituents, -hetero ring which may have one or more substituents or —NRaRb, or it may form a group represented by the following formula together with the adjacent group —N(-A)—X—,

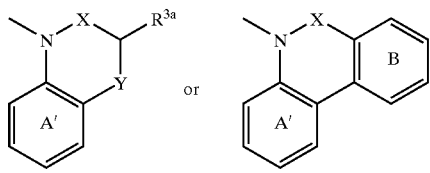

Y: O,S, a bond or CH₂, R³ᵃ: —H, -cycloalkyl which may have one or more substituents, -cycloalkenyl which may have one or more substituents, -aryl which may have one or more substituents or -hetero ring which may have one or more substituents, and A' and B: the same or different from each other, and each represents benzene ring which may have one or more substituents).

2. The amide derivative or a salt thereof according to claim 1, wherein R¹ and R² may be the same or different from each other and each represents —H, -lower alkyl, -lower alkenyl, -lower alkynyl, —NRaRb, —NRc-NRaRb, -(nitrogen-containing saturated heterocyclic ring which may be substituted with lower alkyl), —NRc-C(=NH) NRaRb, NRaCORb, —NRaCO—ORb, —NRaCO—NRbRc, —NRaCO-lower alkylene-NRbRc or —NRaCO-lower alkylene-(nitrogen-containing saturated heterocyclic ring which may be substituted with lower alkyl), A is, aryl which may have 1 to 5 substituents selected from a group D, heteroaryl which may have 1 to 5 substituents selected from the group D, saturated carbon ring-condensed aryl which may have 1 to 5 substituents selected from the group D or saturated heterocyclic ring-condensed aryl which may have 1 to 5 substituents selected from the group D, and R³ is cycloalkyl which may have 1 to 5 substituents selected from the group D, cycloalkenyl which may have 1 to 5 substituents selected from the group D, aryl which may have 1 to 5 substituents selected from the group D, saturated carbon ring-condensed aryl which may have 1 to 5 substituents selected from the group D, saturated heterocyclic ring-condensed aryl which may have 1 to 5 substituents selected from the group D, heteroaryl which may have 1 to 5 substituents selected from the group D or 5- to 8-membered monocyclic saturated heterocyclic ring which may have 1 to 5 substituents selected from the group D, wherein the group D represents -(lower alkyl which y have 1 or 2 substituents selected from —ORa, —SRa, —CN, —COORa, —CONRaRb, —NRaRb and -(nitrogen-containing saturated heterocyclic ring which may have one or more substituents selected from -lower alkyl, -lower alkylene-COORa and —NRaRb), -lower alkenyl, -lower alkynyl, -halogeno lower alkyl, 5- or 6-membered monocyclic heteroaryl, -cycloalkyl, -cycloalkenyl, -aryl, —NRaRb —NRc—NRaRb, -(nitrogen-containing saturated heterocyclic ring which may have one or more substituents selected from -lower alkyl, -lower alkylene-COORa and —NRaRb),

94

—NRc-(nitrogen-containing saturated heterocyclic ring which may have one or more substituents selected from -lower alkyl, -lower alkylene-COORa and NRaRb), O-lower alkylene- NRaRb, —O-lower alkylene-(nitrogen-containing saturated heterocyclic ring which may have one or more substituents selected from -lower alkyl, -lower alkylene-COORa and —NRaRb), —O-lower alkylene-ORa, —O-lower alkyl-COORa, —COORa, -halogen, —CORa, —NO₂, —CN, —ORa, —O-(halogeno lower alkyl), —SRa, —SORa, —SO₂Ra, —CO—NRaRb, —CO-(nitrogen-containing saturated heterocyclic ring which may have one or more substituents selected from -lower alkyl, -lower alkylene-COORa and —NRaRb), —NRa—CORb, —SO₂NRaRb or =O(oxo).

3. The amide derivative or a salt thereof according to claim 1, wherein X is CO.

4. The amide derivative or a salt thereof according to claim 1, wherein R¹ is —NH₂ and R² is —H.

5. The amide derivative or a salt thereof according to claim 1, wherein it is selected from N-({[4-(2-Aminothiazol-4-yl)phenyl]carbamoyl}methyl)-4-fluoro-N-(2,3-dihydro- 1H-indol-6-yl)benzamide; N-({[4-(2-aminothiazol-4-yl-)phenyl]carbamoyl}methyl)-4-fluoro-N-(1,2,3,4-tetradihydroquinolin-6-yl)benzamide; N-({[4-(2-aminothiazol-4-yl)phenyl]carbamoyl}methyl)-N-(2,3-dihydro-1,4-benzodioxin-6-yl)-4-fluorobenzamide; N-({[4-(2-aminothiazol-4-yl)phenyl]carbamoyl}methyl)-N-(1,3-benzodioxol-5yl)-4-fluorobenzamide; N-({[4-(2-aminothiazol-4-yl)phenyl]carbamoyl}methyl)-N-benzothiazol-5-yl-4-fluorobenzamide; N-({[4-(2-aminothiazol-4-yl)phenyl]carbamoyl}methyl)-N-benzothiazol-6-yl-4-fluorobenzamide; N-({[4-(2-aminothiazol-4-yl)phenyl]carbamoyl}methyl)-4-fluoro-N-indan-5-ylbenzamide; N-({[4-(2-aminothiazol-4-yl)phenyl]carbamoyl}methyl)-4-fluoro-N-(3-hydroxyindan-5-yl)benzamide; N-({[4-(2-aminothiazol-4-yl)phenyl]carbamoyl}methyl)-4-fluoro-N-(1H-indol-5-yl)benzamide; N-({[4-(2-aminothiazol-4-yl)phenyl]carbamoyl}methyl)-4-fluoro-N-(3-oxo-3,4-dihydro-2H-1,4-benzothiazin-6-yl)benzamide; N-({[4-(2-aminothiazol-4-yl)phenyl]carbamoyl}methyl)-4-fluoro-N-(3-oxo-3,4-dihydro-2H- 1,4-benzoxazin-6-yl )benzamide; N-({[4-(2-aminothiazol-4-yl)phenyl]carbamoyl}methyl)-N-(1,2,3-benzothiadiazol-5-yl)-4-fluorobenzamide; N-({[4-(2-aminothiazol-4-yl)phenyl]carbamoyl}methyl)-N-(4-methoxyphenyl)tetrahydro-2H-thiopyran-4-carboxamide 1,1-dioxide; N-({[4-(2-aminothiazol-4-yl)phenyl]carbamoyl}methyl)-N-benzothiazol-5-yl-4-fluorocyclohex-3-enecarboxamide; N-({[4-(2-aminothiazol-4-yl)phenyl]carbamoyl}methyl)-N-benzothiazol-5-yl-4,4-difluorocyclohexanecarboxamide; and N-({[4-(2-aminothiazol-4-yl)phenyl]carbamoyl}methyl)-N-indan-5-yltetrahydro-2H-thiopyran-4-carboxamide 1,1-dioxide.

6. A pharmaceutical composition which comprises the amide derivative or a salt thereof described in claim 1 and a pharmacologically acceptable carrier.

7. The pharmaceutical composition according to claim 6, wherein it is an anti-herpesvirus agent.

8. The pharmaceutical composition according to claim 7, wherein it is an anti-varicella zoster virus agent.

* * * * *